(12) United States Patent
Zhamu et al.

(10) Patent No.: US 9,988,273 B2
(45) Date of Patent: Jun. 5, 2018

(54) PROCESS FOR PRODUCING HIGHLY ORIENTED HUMIC ACID FILMS AND HIGHLY CONDUCTING GRAPHITIC FILMS DERIVED THEREFROM

(71) Applicant: Nanotek Instruments, Inc., Dayton, OH (US)

(72) Inventors: Aruna Zhamu, Springboro, OH (US); Bor Z Jang, Centerville, OH (US)

(73) Assignee: Nanotek Instruments, Inc., Dayton, OH (US)

( * ) Notice: Subject to any disclaimer, the term of this patent is extended or adjusted under 35 U.S.C. 154(b) by 183 days.

(21) Appl. No.: 15/240,543

(22) Filed: Aug. 18, 2016

(65) Prior Publication Data

US 2018/0050914 A1    Feb. 22, 2018

(51) Int. Cl.

| C01B 32/182 | (2017.01) |
| C01B 31/04 | (2006.01) |
| C09K 5/14 | (2006.01) |
| H01B 1/04 | (2006.01) |
| C07D 413/14 | (2006.01) |

(52) U.S. Cl.
CPC ............ *C01B 31/04* (2013.01); *C07D 413/14* (2013.01); *C09K 5/14* (2013.01); *H01B 1/04* (2013.01)

(58) Field of Classification Search
CPC ...... C07D 413/14; C01B 32/182; B82Y 40/00
See application file for complete search history.

(56) References Cited

U.S. PATENT DOCUMENTS

| 6,872,330 B2 | 3/2005 | Mack |
| 6,913,154 B2 | 7/2005 | Koslow |
| 7,071,258 B1 | 7/2006 | Jang |
| 7,327,000 B2 | 2/2008 | DeHeer |

(Continued)

FOREIGN PATENT DOCUMENTS

| CN | 1230972 A | 10/1999 |
| CN | 103641117 A | 3/2014 |

(Continued)

OTHER PUBLICATIONS

Duraia et al., "Reduced humic acid nanosheets and its uses as nanofiller", 2015, J. Phys. Chem. Soilids, 85, pp. 86-90. (Year: 2015).*

(Continued)

*Primary Examiner* — Robert A Vetere

(57) ABSTRACT

A process for producing a highly oriented humic acid (HA) film, comprising: (a) preparing a dispersion of HA or chemically functionalized HA (CHA) sheets dispersed in a liquid medium, wherein HA sheets contain an oxygen content higher than 5% by weight or CHA sheets contain non-carbon element content higher than 5% by weight; (b) dispensing and depositing HA or CHA dispersion onto a surface of a supporting substrate to form a wet layer, under an orientation-inducing stress; (c) removing liquid medium from the wet layer to form a dried HA or CHA layer having hexagonal carbon planes and an inter-planar spacing $d_{002}$ of 0.4 nm to 1.3 nm as determined by X-ray diffraction; and (d) thermally reducing the dried HA or CHA layer at a first heat treatment temperature higher than 80° C. for a sufficient period of time to produce the film containing reduced HA or CHA.

31 Claims, 12 Drawing Sheets

(56) References Cited

U.S. PATENT DOCUMENTS

| | | | |
|---|---|---|---|
| 7,623,340 B1 | 11/2009 | Song | |
| 7,948,739 B2 | 5/2011 | Zhamu | |
| 9,053,870 B2 | 6/2015 | Yu et al. | |
| 9,233,850 B2 | 1/2016 | Jang | |
| 2005/0271574 A1 | 12/2005 | Jang | |
| 2008/0048152 A1 | 2/2008 | Jang | |
| 2009/0061312 A1 | 3/2009 | Zhamu | |
| 2010/0021819 A1 | 1/2010 | Zhamu | |
| 2011/0201739 A1* | 8/2011 | Beall | B82Y 30/00 524/325 |
| 2013/0095389 A1 | 4/2013 | Bhardwaj et al. | |
| 2014/0315083 A1 | 10/2014 | Liu et al. | |

FOREIGN PATENT DOCUMENTS

| | | |
|---|---|---|
| CN | 104600320 A | 5/2015 |
| CN | 103752281 B | 4/2016 |
| WO | 2012151880 A1 | 11/2012 |

OTHER PUBLICATIONS

Bor Z. Jang and A. Zhamu, "Processing of Nano Graphene Platelets (NGPs) and NGP Nanocomposites: A Review," J. Materials Sci. 43 (2008) 5092-5101.

William S. Hummers, Jr., et al., Preparation of Graphitic Oxide, Journal of the American Chemical Society, 1958, p. 1339.

Yang, et al. "Two-dimensional Graphene Nano-ribbons," J. Am. Chem. Soc. 130 (2008) 4216-17.

Y. Xu, et al. "Self-Assembled Graphene Hydrogel via a One-Step Hydrothermal Process," ACS Nano 2010, 4, 4324-4330.

Zongping Chen, et al., "Three-dimensional flexible and conductive interconnected graphene networks grown by chemical vapour deposition," Nature Materials, 10 (Jun. 2011) 424-428.

B. G. Choi, et al., "3D Macroporous Graphene Frameworks for Supercapacitors with High Energy and Power Densities," ACS Nano, 6 (2012) 4020-4028.

Stevenson F.J. "Humus Chemistry: Genesis, Composition, Reactions," John Wiley & Sons, New York 1994.

G. W. Anderson, et al., J. Amer. Chem. Soc. 96, 1839 (1965).

Anderson et al., "The Use of Esters of N-Hydroxysuccinimide in Peptide Synthesis" J. Amer. Chem. Soc. (1964) vol. 86, No. 9, pp. 1839-1842.

Stevenson, Humus Chemistry: Genesis, Composition, Reactions (1982) pp. 258-263, John Wiley & Sons, New York.

PCT/US17/43485, International Search Report and Written Opinion dated Sep. 27, 2017, 10 pages.

CN 103641117a, Google Patent English language translation, 5 pages.

CN 103752281B, Google Patent English language translation, 8 pages.

CN 104600320A Google Patent English Translation, 6 pages.

CN 1230972A, Google Patents English language translation, 22 pages.

PCT/US17/18708 International Search Report and Written Opinion dated Jun. 6, 2017, 12 pages.

PCT/US17/36032 International Search Report and Written Opinion dated Aug. 25, 2017, 11 pages.

Porada et al., "Review on the science and technology of water desalination by capacitive deionization" Progress in Materials Science (2013) vol. 58, pp. 1388-1442.

U.S. Appl. No. 15/243,589 Nonfinal Office Action dated Nov. 16, 2017, 8 pages.

U.S. Appl. No. 15/243,589 Response Nonfinal Office Action dated Nov. 22, 2017, 11 pages.

U.S. Appl. No. 15/251,849 Nonfinal Office Action dated Nov. 1, 2017, 21 pages.

U.S. Appl. No. 15/270,868 Nonfinal Office Action dated Nov. 1, 2017, 23 pages.

* cited by examiner

20 μm (50 μm wide)

PROCESS FOR PRODUCING HIGHLY ORIENTED HUMIC ACID FILMS AND HIGHLY CONDUCTING GRAPHITIC FILMS DERIVED THEREFROM

FIELD OF THE INVENTION

The present invention relates generally to the field of graphitic materials and, more particularly, to a process for producing a highly oriented humic acid film and a graphitic film derived therefrom. This new thin-film material exhibits an unprecedented combination of exceptionally high thermal conductivity, high electrical conductivity, and high tensile strength.

BACKGROUND OF THE INVENTION

Carbon is known to have five unique crystalline structures, including diamond, fullerene (0-D nano graphitic material), carbon nano-tube or carbon nano-fiber (1-D nano graphitic material), graphene (2-D nano graphitic material), and graphite (3-D graphitic material). The carbon nano-tube (CNT) refers to a tubular structure grown with a single wall or multi-wall. Carbon nano-tubes (CNTs) and carbon nano-fibers (CNFs) have a diameter on the order of a few nanometers to a few hundred nanometers. Their longitudinal, hollow structures impart unique mechanical, electrical and chemical properties to the material. The CNT or CNF is a one-dimensional nano carbon or 1-D nano graphite material.

Bulk natural graphite is a 3-D graphitic material with each graphite particle being composed of multiple grains (a grain being a graphite single crystal or crystallite) with grain boundaries (amorphous or defect zones) demarcating neighboring graphite single crystals. Each grain is composed of multiple graphene planes that are oriented parallel to one another. A graphene plane in a graphite crystallite is composed of carbon atoms occupying a two-dimensional, hexagonal lattice. In a given grain or single crystal, the graphene planes are stacked and bonded via van der Waal forces in the crystallographic c-direction (perpendicular to the graphene plane or basal plane). Although all the graphene planes in one grain are parallel to one another, typically the graphene planes in one grain and the graphene planes in an adjacent grain are inclined at different orientations. In other words, the orientations of the various grains in a graphite particle typically differ from one grain to another.

A graphite single crystal (crystallite) per se is anisotropic with a property measured along a direction in the basal plane (crystallographic a- or b-axis direction) being dramatically different than if measured along the crystallographic c-axis direction (thickness direction). For instance, the thermal conductivity of a graphite single crystal can be up to approximately 1,920 W/mK (theoretical) or 1,800 W/mK (experimental) in the basal plane (crystallographic a- and b-axis directions), but that along the crystallographic c-axis direction is less than 10 W/mK (typically less than 5 W/mK). Further, the multiple grains or crystallites in a graphite particle are typically all oriented along different directions. Consequently, a natural graphite particle composed of multiple grains of different orientations exhibits an average property between these two extremes (i.e. typically not much higher than 5 W/mK).

It would be highly desirable in many applications to produce a thin graphitic structure having sufficiently large lateral dimensions (i.e. large length and width) and having all graphene planes (or hexagonal carbon planes) being essentially parallel to one another along one desired direction. In other words, it is highly desirable to have one large-size graphitic film (e.g. a fully integrated layer of multiple graphene planes) having the c-axis directions of all the graphene planes being substantially parallel to one another and having a sufficiently large length and/or width for a particular application. Up to this point of time, it has been extremely difficult to produce such a highly oriented graphitic film. Even though some attempts have been made to produce the so-called highly oriented pyrolytic graphite (HOPG) through tedious, energy intensive, and expensive chemical vapor deposition (CVD) followed by ultra-high temperature graphitization, the graphitic structure of the HOPG remains inadequately aligned and, hence, exhibits properties that are significantly lower than what is theoretically predicted.

The present invention is directed at a new materials science approach to designing and building a new class of materials, herein referred to as the highly oriented humic acid film (HOHA film), from humic acid alone or a combination of humic acid and graphene (including graphene oxide, graphene fluoride, nitrogenated graphene, hydrogenated graphene, boron-doped graphene, other types of doped graphene, and other types of chemically functionalized graphene). A HOHA is a thin-film structure composed of highly aligned humic acid molecules or their derivatives (graphene- or graphene oxide-like 2D planes of hexagonal carbon atoms), wherein all of the graphene- or graphene oxide-like planes are essentially parallel to one another. These hexagonal carbon planes are much better aligned than what the conventional HOPG has been able to achieve. Such a HOHA film has a thickness typically from 5 nm to 500 µm, but more typically from 10 nm to 200 µm, further more typically and preferably from 100 nm to 100 µm. In most cases, the HOGF has an oxygen amount of 0.01-5% by weight, but can be almost oxygen-free. The conventional HOPG contains no oxygen.

The constituent graphene planes of a graphite crystallite in a natural or artificial graphite particle can be exfoliated and extracted or isolated to obtain individual graphene sheets of carbon atoms provided the inter-planar van der Waals forces can be overcome. An isolated, individual graphene sheet of carbon atoms is commonly referred to as single-layer graphene. A stack of multiple graphene planes bonded through van der Waals forces in the thickness direction with an inter-graphene plane spacing of approximately 0.3354 nm is commonly referred to as a multi-layer graphene. A multi-layer graphene platelet has up to 300 layers of graphene planes (<100 nm in thickness), but more typically up to 30 graphene planes (<10 nm in thickness), even more typically up to 20 graphene planes (<7 nm in thickness), and most typically up to 10 graphene planes (commonly referred to as few-layer graphene in scientific community). Single-layer graphene and multi-layer graphene sheets are collectively called "nano graphene platelets" (NGPs). Graphene or graphene oxide sheets/platelets (collectively, NGPs) are a new class of carbon nano material (a 2-D nano carbon) that is distinct from the 0-D fullerene, the 1-D CNT, and the 3-D graphite.

Our research group pioneered the development of pristine graphene materials, isolated graphene oxide sheets, and related production processes as early as 2002: (1) B. Z. Jang and W. C. Huang, "Nano-scaled Graphene Plates," U.S. Pat. No. 7,071,258 (Jul. 4, 2006), application submitted on Oct. 21, 2002; (2) B. Z. Jang, et al. "Process for Producing Nano-scaled Graphene Plates," U.S. patent application Ser. No. 10/858,814 (Jun. 3, 2004); and (3) B. Z. Jang, A. Zhamu, and J. Guo, "Process for Producing Nano-scaled Platelets and Nanocomposites," U.S. patent application Ser. No. 11/509,424 (Aug. 25, 2006). Historically, Brodie first demonstrated the synthesis of graphite oxide in 1859 by adding a portion of potassium chlorate to a slurry of graphite in fuming nitric acid. In 1898, Staudenmaier improved on this procedure by using concentrated sulfuric acid as well as fuming nitric acid and adding the chlorate in multiple aliquots over the course of the reaction. This small change in the procedure made the production of highly oxidized graphite in a single reaction vessel significantly more practical. In 1958, Hummers reported the method most commonly used today: the graphite is oxidized by treatment with $KMnO_4$ and $NaNO_3$ in concentrated $H_2SO_4$. However, these earlier work failed to isolate and identify fully exfoliated and separated graphene oxide sheets. These studies also failed to disclose the isolation of pristine, non-oxidized single-layer or multiple-layer graphene sheets.

In real practice (e.g. as illustrated in FIG. 1), NGPs are typically obtained by intercalating natural graphite particles 100 with a strong acid and/or oxidizing agent to obtain a graphite intercalation compound 102 (GIC) or graphite oxide (GO). The presence of chemical species or functional groups in the interstitial spaces between graphene planes serves to increase the inter-graphene spacing ($d_{002}$, as determined by X-ray diffraction), thereby significantly reducing the van der Waals forces that otherwise hold graphene planes together along the c-axis direction. The GIC or GO is most often produced by immersing natural graphite powder in a mixture of sulfuric acid, nitric acid (an oxidizing agent), and another oxidizing agent (e.g. potassium permanganate or sodium perchlorate). The resulting GIC (102) is actually some type of graphite oxide (GO) particles. This GIC or GO is then repeatedly washed and rinsed in water to remove excess acids, resulting in a graphite oxide suspension or dispersion, which contains discrete and visually discernible graphite oxide particles dispersed in water. There are two processing routes to follow after this rinsing step:

Route 1 involves removing water from the suspension to obtain "expandable graphite," which is essentially a mass of dried GIC or dried graphite oxide particles. Upon exposure of expandable graphite to a temperature in the range of typically 800-1,050° C. for approximately 30 seconds to 2 minutes, the GIC undergoes a rapid volume expansion by a factor of 30-300 to form "graphite worms" (104), which are each a collection of exfoliated, but largely un-separated graphite flakes that remain interconnected.

In Route 1A, these graphite worms (exfoliated graphite or "networks of interconnected/non-separated graphite flakes") can be re-compressed to obtain flexible graphite sheets or foils (106) that typically have a thickness in the range of 0.1 mm (100 μm)-0.5 mm (500 μm). Alternatively, one may choose to use a low-intensity air mill or shearing machine to simply break up the graphite worms for the purpose of producing the so-called "expanded graphite flakes" (108) which contain mostly graphite flakes or platelets thicker than 100 nm (hence, not a nano material by definition). These expanded graphite flakes may be made into a paper-like graphite mat (110).

Exfoliated graphite worms, expanded graphite flakes, and the recompressed mass of graphite worms (commonly referred to as flexible graphite sheet or flexible graphite foil) are all 3-D graphitic materials that are fundamentally different and patently distinct from either the 1-D nano carbon material (CNT or CNF) or the 2-D nano carbon material (graphene sheets or platelets, NGPs). Flexible graphite (FG) foils can be used as a heat spreader material, but exhibiting a maximum in-plane thermal conductivity of typically less than 500 W/mK (more typically <300 W/mK) and in-plane electrical conductivity no greater than 1,500 S/cm. These low conductivity values are a direct result of the many defects, wrinkled or folded graphite flakes, interruptions or gaps between graphite flakes, and non-parallel flakes (e.g. SEM image in FIG. 2). Many flakes are inclined with respect to one another at a very large angle (e.g. mis-orientation of 20-40 degrees).

In Route 1B, the exfoliated graphite is subjected to high-intensity mechanical shearing (e.g. using an ultrasonicator, high-shear mixer, high-intensity air jet mill, or high-energy ball mill) to form separated single-layer and multi-layer graphene sheets (collectively called NGPs, 112), as disclosed in our U.S. application Ser. No. 10/858,814. Single-layer graphene can be as thin as 0.34 nm, while multi-layer graphene can have a thickness up to 100 nm, but more typically less than 20 nm. Graphene sheets or platelets may then be made into a graphene paper or membrane (114).

Route 2 entails ultrasonicating the graphite oxide suspension for the purpose of separating/isolating individual graphene oxide sheets from graphite oxide particles. This is based on the notion that the inter-graphene plane separation has been increased from 0.3354 nm in natural graphite to 0.6-1.1 nm in highly oxidized graphite oxide, significantly weakening the van der Waals forces that hold neighboring planes together. Ultrasonic power can be sufficient to further separate graphene plane sheets to form separated, isolated, or discrete graphene oxide (GO) sheets. These graphene oxide sheets can then be chemically or thermally reduced to obtain "reduced graphene oxides" (RGO) typically having an oxygen content of 0.001%-10% by weight, more typically 0.01%-5% by weight, most typically and preferably less than 2% by weight.

For the purpose of defining the claims of the instant application, NGPs include discrete sheets/platelets of single-layer and multi-layer pristine graphene, graphene oxide, or reduced graphene oxide (RGO). Pristine graphene has essentially 0% oxygen. RGO typically has an oxygen content of 0.001%-5% by weight. Graphene oxide (including RGO) can have 0.001%-50% by weight of oxygen.

It may be noted that flexible graphite foils (obtained by compressing or roll-pressing exfoliated graphite worms) for electronic device thermal management applications (e.g. as a heat sink material) have the following major deficiencies: (1) As indicated earlier, flexible graphite (FG) foils exhibit a relatively low thermal conductivity, typically <500 W/mK and more typically <300 W/mK. By impregnating the exfoliated graphite with a resin, the resulting composite exhibits an even lower thermal conductivity (typically <<200 W/mK, more typically <100 W/mK). (2) Flexible graphite foils, without a resin impregnated therein or coated thereon, are of low strength, low rigidity, and poor structural integrity. The high tendency for flexible graphite foils to get torn apart makes them difficult to handle in the process of making a heat sink. As a matter of fact, the flexible graphite sheets (typically 50-200 μm thick) are so "flexible" that they are not sufficiently rigid to make a fin component material for a finned heat sink. (3) Another very subtle, largely ignored or overlooked, but critically important feature of FG foils is their high tendency to get flaky with graphite flakes easily coming off from FG sheet surfaces and emitting out to other parts of a microelectronic device. These highly electrically conducting flakes (typically 1-200 μm in lateral dimensions and >100 nm in thickness) can cause internal shorting and failure of electronic devices.

Similarly, solid NGPs (including discrete sheets/platelets of pristine graphene, GO, and RGO), when packed into a film, membrane, or paper sheet (114) of non-woven aggregates using a paper-making process, typically do not exhibit a high thermal conductivity unless these sheets/platelets are closely packed and the film/membrane/paper is ultra-thin (e.g. <1 μm, which is mechanically weak). This is reported in our earlier U.S. patent application Ser. No. 11/784,606 (Apr. 9, 2007). However, ultra-thin film or paper sheets (<10 μm) are difficult to produce in mass quantities, and difficult to handle when one tries to incorporate these thin films as a heat sink material. In general, a paper-like structure or mat made from platelets of graphene, GO, or RGO (e.g. those paper sheets prepared by vacuum-assisted filtration process) exhibit many defects, wrinkled or folded graphene sheets, interruptions or gaps between platelets, and non-parallel platelets (e.g. SEM image in FIG. 3(B)), leading to relatively poor thermal conductivity, low electric conductivity, and low structural strength. These papers or aggregates of discrete NGP, GO or RGO platelets alone (without a resin binder) also have a tendency to get flaky, emitting conductive particles into air.

Another prior art graphitic material is the pyrolytic graphite film, typically thinner than 100 μm. The process begins with carbonizing a polymer film (e.g. polyimide) at a carbonization temperature of 400-1,500° C. under a typical pressure of 10-15 Kg/cm$^2$ for 10-36 hours to obtain a carbonized material, which is followed by a graphitization treatment at 2,500-3,200° C. under an ultrahigh pressure of 100-300 Kg/cm$^2$ for 1-24 hours to form a graphitic film. It is technically utmost challenging to maintain such an ultrahigh pressure at such an ultrahigh temperature. This is a difficult, slow, tedious, energy-intensive, and extremely expensive process. Furthermore, it has been difficult to produce pyrolytic graphite film thinner than 10 μm or thicker than 100 μm from a polymer such as polyimide. This thickness-related problem is inherent to this class of materials due to their difficulty in forming into an ultra-thin (<10 μm) and thick film (>100 μm) while still maintaining an acceptable degree of polymer chain orientation and mechanical strength that are required of proper carbonization and graphitization.

A second type of pyrolytic graphite is produced by high temperature decomposition of hydrocarbon gases in vacuum followed by deposition of the carbon atoms to a substrate surface. This vapor phase condensation of cracked hydrocarbons is essentially a chemical vapor deposition (CVD) process. In particular, highly oriented pyrolytic graphite (HOPG) is the material produced by subjecting the CVD-deposited pyro-carbon to a uniaxial pressure at very high temperatures (typically 3,000-3,300° C.). This entails a thermo-mechanical treatment of combined and concurrent mechanical compression and ultra-high temperature for an extended period of time in a protective atmosphere; a very expensive, energy-intensive, time-consuming, and technically challenging process. The process requires ultra-high temperature equipment (with high vacuum, high pressure, or high compression provision) that is not only very expensive to make but also very expensive and difficult to maintain. Even with such extreme processing conditions, the resulting HOPG still possesses many defects, grain boundaries, and mis-orientations (neighboring graphene planes not parallel to each other), resulting in less-than-satisfactory in-plane properties. Typically, the best prepared HOPG sheet or block typically contains many poorly aligned grains or crystals and a vast amount of grain boundaries and defects.

Similarly, the most recently reported graphene thin film (<2 nm) prepared by catalytic CVD of hydrocarbon gas (e.g. $C_2H_4$) on Ni or Cu surface is not a single-grain crystal, but a poly-crystalline structure with many grain boundaries and defects. With Ni or Cu being the catalyst, carbon atoms obtained via decomposition of hydrocarbon gas molecules at 800-1,000° C. are deposited onto Ni or Cu foil surface to form a sheet of single-layer or few-layer graphene that is poly-crystalline. The grains are typically much smaller than 100 μm in size and, more typically, smaller than 10 μm in size. These graphene thin films, being optically transparent and electrically conducting, are intended for applications such as the touch screen (to replace indium-tin oxide or ITO glass) or semiconductor (to replace silicon, Si). Furthermore, the Ni- or Cu-catalyzed CVD process does not lend itself to the deposition of more than 5 graphene planes (typically <2 nm) beyond which the underlying Ni or Cu catalyst can no longer provide any catalytic effect. There has been no experimental evidence to indicate that CVD graphene layer thicker than 5 nm is possible. Both CVD graphene film and HOPG are extremely expensive.

The above discussion clearly indicates that every prior art method or process for producing graphene and graphitic thin film has major deficiencies. Hence, an urgent need exists to have a new class of carbon nano materials that are comparable or superior to graphene in terms of properties, but can be produced more cost-effectively, faster, more scalable, and in a more environmentally benign manner. The production process for such a new carbon nano material must require a reduced amount of undesirable chemical (or elimination of these chemicals all together), shortened process time, less energy consumption, reduced or eliminated effluents of undesirable chemical species into the drainage (e.g., sulfuric acid) or into the air (e.g., $SO_2$ and $NO_2$). Furthermore, one should be able to readily make this new nano material into a thin film graphitic structure that is relatively conductive, both thermally and electrically.

Thus, it is an object of the present invention to provide a new class of thin film graphitic material (from 5 nm to 500 μm in thickness) that is thermally and electrically conducting and mechanically robust and to provide a cost-effective method of producing this new class of graphitic film.

Humic acid (HA) is an organic matter commonly found in soil and can be extracted from the soil using a base (e.g. KOH). HA can also be extracted, with a high yield, from a type of coal called leonardite, which is a highly oxidized version of lignite coal. HA extracted from leonardite contains a number of oxygenated groups (e.g. carboxyl groups) located around the edges of the graphene-like molecular center ($SP^2$ core of hexagonal carbon structure). This material is slightly similar to graphene oxide (GO) which is produced by strong acid oxidation of natural graphite. HA has a typical oxygen content of 5% to 42% by weight (other major elements being carbon and hydrogen). HA, after chemical or thermal reduction, has an oxygen content of 0.01% to 5% by weight. For claim definition purposes in the instant application, humic acid (HA) refers to the entire oxygen content range, from 0.01% to 42% by weight. The reduced humic acid (RHA) is a special type of HA that has an oxygen content of 0.01% to 5% by weight.

The present invention provides a new class of graphene-like 2D materials (i.e. humic acid) that surprisingly can be used alone or in a combination with graphene to form a graphitic film. Thus, another object of the present invention is to provide a cost-effective method of producing such a humic acid or humic acid-graphene hybrid film-derived graphitic films in large quantities. This method or process does not involve the use of an environmentally unfriendly chemical. The humic acid- or humic acid/graphene-derived graphitic films exhibit a thermal conductivity, electrical conductivity, elastic modulus, and/or strength comparable to or greater than those of the conventional highly oriented pyrolytic graphite films. This process is capable of producing a highly oriented graphitic film of practically any desired thickness, from several nanometers (nm) to several hundred micrometers (μm).

Another object of the present invention is to provide products (e.g. devices) that contain graphitic films of the present invention and methods of operating these products. The product can be a heat dissipation element in a smart phone, tablet computer, digital camera, display device, flat-panel TV, LED lighting device, etc. Such a thin film exhibits a combination of exceptional thermal conductivity, electrical conductivity, mechanical strength, and elastic modulus unmatched by any material of comparable thickness range. The highly oriented graphitic film can exhibit an electrical conductivity greater than 12,000 S/cm, a thermal conductivity greater than 1,500 W/mK, a physical density greater than 2.1 g/cm$^3$, a tensile strength greater than 120 MPa, and/or an elastic modulus greater than 120 GPa. No other material is known to exhibit this set of outstanding properties.

SUMMARY OF THE INVENTION

The present invention provides a process for producing a highly oriented humic acid film (with or without externally added graphene sheets) and humic acid-derived graphitic film with a thickness from 5 nm to 500 μm and a physical density no less than 1.3 g/cm$^3$ (more typically >1.5 g/cm$^3$ and further more typically >1.6 g/cm$^3$). The process comprises (a) preparing a dispersion of humic acid (HA) or chemically functionalized humic acid (CHA) having HA or CHA sheets dispersed in a liquid medium, wherein the HA sheets contain an oxygen content higher than 5% by weight or the CHA sheets contain non-carbon element content higher than 5% by weight; (b) dispensing and depositing the HA or CHA dispersion onto a surface of a supporting substrate to form a wet layer of HA or CHA, wherein the dispensing and depositing procedure includes subjecting the dispersion to an orientation-inducing stress; (c) partially or completely removing the liquid medium from the wet layer of HA or CHA to form a dried HA or CHA layer having hexagonal carbon planes and an inter-planar spacing $d_{002}$ of 0.4 nm to 1.3 nm as determined by X-ray diffraction; and (d) heat-treating the dried HA or CHA layer at a first heat treatment temperature higher than 80° C. for a sufficient period of time to produce the highly oriented humic acid film containing interconnected/merged HA/CHA molecules or thermally reduced HA or CHA sheets that are substantially parallel to one another. This highly oriented humic acid film of interconnected or merged HA or CHA sheets may be subjected to an additional step of compressing.

The process (with or without the step of compressing) can further comprise a step (e) of further heat-treating the humic acid film of reduced HA or CHA at a second heat treatment temperature higher than the first heat treatment temperature for a sufficient period of time to produce a graphitic film having an inter-planar spacing $d_{002}$ less than 0.4 nm and an oxygen content or non-carbon element content less than 5% by weight; and (f) compressing said graphitic film to produce a highly conducting graphitic film.

In certain preferred embodiments, the HA or CHA dispersion further contains graphene sheets or molecules dispersed therein and the HA-to-graphene or CHA-to-graphene ratio is from 1/100 to 100/1 and these graphene sheets are selected from pristine graphene, graphene oxide, reduced graphene oxide, graphene fluoride, graphene bromide, graphene iodide, boron-doped graphene, nitrogen-doped graphene, chemically functionalized graphene, or a combination thereof.

In some embodiments, HA or CHA sheets are in an amount sufficient to form a liquid crystal phase in said liquid medium. In certain specific embodiments, the dispersion contains a first volume fraction of HA or CHA dispersed in the liquid medium that exceeds a critical volume fraction ($V_c$) for a liquid crystal phase formation and the dispersion is concentrated to reach a second volume fraction of HA or CHA, greater than the first volume fraction, to improve a HA or CHA sheet orientation. The first volume fraction may be equivalent to a weight fraction of from 0.05% to 3.0% by weight of HA or CHA in the dispersion. The dispersion may be concentrated to contain higher than 3.0% but less than 15% by weight of HA or CHA dispersed in said liquid medium prior to said step (b).

In general, the dispersion does not contain any other polymer than the HA or CHA itself. However, in some embodiments, the dispersion may further contain a polymer dissolved in the liquid medium or attached to the HA or CHA.

In certain embodiments, CHA or the externally added graphene sheets (if any), or both, contains a chemical functional group selected from a polymer, $SO_3H$, COOH, $NH_2$, OH, R'CHOH, CHO, CN, COCl, halide, COSH, SH, COOR', SR', SiR'$_3$, Si(—OR'—)$_y$R'$_3$-y, Si(—O—SiR'$_2$—) OR', R", Li, AlR'$_2$, Hg—X, TlZ$_2$ and Mg—X; wherein y is an integer equal to or less than 3, R' is hydrogen, alkyl, aryl, cycloalkyl, or aralkyl, cycloaryl, or poly(alkylether), R" is fluoroalkyl, fluoroaryl, fluorocycloalkyl, fluoroaralkyl or cycloaryl, X is halide, and Z is carboxylate or trifluoroacetate, or a combination thereof.

The second heat treatment temperature may be higher than 1,500° C. for a length of time sufficient for decreasing an inter-plane spacing $d_{002}$ to a value less than 0.36 nm and decreasing the oxygen content or non-carbon element content to less than 0.1% by weight. In the invented process, the second heat treatment temperature is preferably from 1,500° C. to 3,200° C.

The liquid medium may contain water and/or an alcohol. The liquid medium may contain a non-aqueous solvent selected from polyethylene glycol, ethylene glycol, propylene glycol, an alcohol, a sugar alcohol, a polyglycerol, a glycol ether, an amine based solvent, an amide based solvent, an alkylene carbonate, an organic acid, or an inorganic acid.

In certain embodiments, the dried layer of HA or CHA has a thickness from 10 nm to 200 μm or the resulting highly conductive graphitic film has a thickness from 10 nm to 200 μm.

Preferably, the process is a roll-to-roll or reel-to-reel process, wherein step (b) includes feeding a sheet of a solid substrate material from a roller to a deposition zone, depositing a layer of HA or CHA dispersion onto a surface of the sheet of solid substrate material to form the wet layer of HA or CHA dispersion thereon, drying the HA or CHA dispersion to form the dried HA or CHA layer deposited on the substrate surface, and collecting the HA or CHA layer-deposited substrate sheet on a collector roller.

In the invented process, the first heat treatment temperature can contain a temperature in the range of 100° C.-1,500° C. and the highly oriented graphene film has an oxygen content less than 2.0%, an inter-planar spacing less than 0.35 nm, a thermal conductivity of at least 800 W/mK, and/or an electrical conductivity no less than 2,500 S/cm.

In some embodiments, the first heat treatment temperature contains a temperature in the range of 1,500° C.-2,100° C. and the highly oriented humic acid film has an oxygen content less than 1.0%, an inter-planar spacing less than 0.345 nm, a thermal conductivity of at least 1,000 W/mK, and/or an electrical conductivity no less than 5,000 S/cm. Preferably, the first and/or second heat treatment temperature contains a temperature greater than 2,100° C. and the highly oriented humic acid film has an oxygen content no greater than 0.001%, an inter-graphene spacing less than 0.340 nm, a mosaic spread value no greater than 0.7, a thermal conductivity of at least 1,300 W/mK, and/or an electrical conductivity no less than 8,000 S/cm.

In the process wherein the dispersion contains both humic acid and graphene, the second heat treatment temperature can contain a temperature no less than 2,500° C. and the highly conducting graphitic film has an inter-graphene spacing less than 0.336 nm, a mosaic spread value no greater than 0.4, a thermal conductivity greater than 1,600 W/mK, and/or an electrical conductivity greater than 10,000 S/cm.

In some embodiments, the process results in the highly oriented humic acid film exhibiting a degree of graphitization no less than 80% and/or a mosaic spread value less than 0.4. Typically, the highly oriented humic acid film contains chemically bonded hexagonal carbon planes that are parallel to one another.

In some embodiments, the starting HA or CHA sheets have a maximum original length and the resulting highly oriented humic acid film contains HA or CHA sheets having a length larger than the maximum original length.

In the invented process involving the addition of some graphene sheets in the dispersion, the highly oriented humic acid film is a poly-crystal graphene structure having a preferred crystalline orientation as determined by said X-ray diffraction method. In the process, step (e) of heat-treating induces chemical linking, merging, or chemical bonding of HA or CHA sheets (with other HA or CHA sheets or with graphene sheets), and/or re-graphitization or re-organization of a graphitic structure.

It is quite surprising to observe that, under the heat treatment temperature conditions, HA/CHA sheets or molecules are capable of reacting or merging with other HA/CHA sheets or molecules and, further surprisingly, these HA/CHA sheets or molecules are capable of reacting or merging with externally added graphene sheets, provided all these HA/CHA sheets/molecules and graphene sheets are well-aligned and packed together so that their molecular planes are essentially parallel to each other. These features enable integration of HA/CHA sheets/molecules and graphene sheets into one monolithic entity, not just an aggregate of separated sheets.

With the presence of externally added graphene sheets in the dispersion, the highly oriented graphitic film has an electrical conductivity greater than 5,000 S/cm, a thermal conductivity greater than 800 W/mK, a physical density greater than 1.9 g/cm$^3$, a tensile strength greater than 80 MPa, and/or an elastic modulus greater than 60 GPa. Preferably and typically, the highly oriented graphitic film has an electrical conductivity greater than 8,000 S/cm, a thermal conductivity greater than 1,200 W/mK, a physical density greater than 2.0 g/cm$^3$, a tensile strength greater than 100 MPa, and/or an elastic modulus greater than 80 GPa. Further preferably, the highly oriented graphitic film has an electrical conductivity greater than 12,000 S/cm, a thermal conductivity greater than 1,500 W/mK, a physical density greater than 2.1 g/cm$^3$, a tensile strength greater than 120 MPa, and/or an elastic modulus greater than 120 GPa.

The present invention also provides a highly oriented graphitic film produced by the presently invented process (with or without externally added graphene sheets in the dispersion). The invention also provides a microelectronic device containing a highly oriented graphitic film of present invention as a heat-dissipating or heat-spreading element. The microelectronic device can be a smart phone, tablet computer, flat-panel display, flexible display, electronic watch, a wearable electronic device, a TV, or a microelectronic communications device.

DESCRIPTION OF THE PREFERRED EMBODIMENTS

Figure 1:
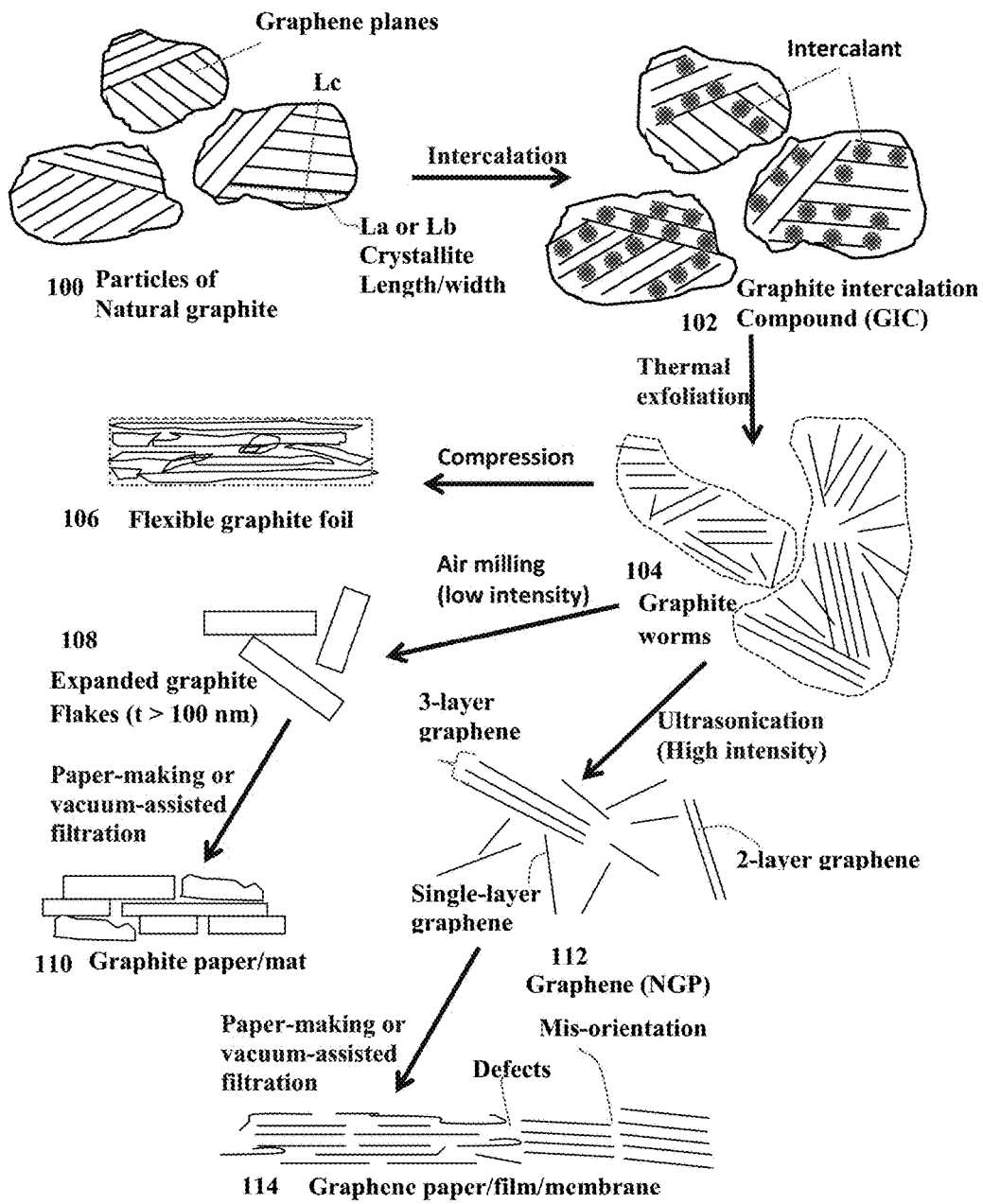
FIG. 1 A flow chart illustrating various prior art processes for producing exfoliated graphite products (flexible graphite foils and flexible graphite composites) and pyrolytic graphite (bottom portion), along with a process for producing isolated graphene sheets and aggregates of graphene or graphene oxide sheets in the form of a graphene paper or membrane.

Humic acid (HA) is an organic matter commonly found in soil and can be extracted from the soil using a base (e.g. KOH). HA can also be extracted from a type of coal called leonardite, which is a highly oxidized version of lignite coal. HA extracted from leonardite contains a number of oxygenated groups (e.g. carboxyl groups) located around the edges of the graphene-like molecular center ($SP^2$ core of hexagonal carbon structure). This material is slightly similar to graphene oxide (GO) which is produced by strong acid oxidation of natural graphite. HA has a typical oxygen content of 5% to 42% by weight (other major elements being carbon, hydrogen, and nitrogen). An example of the molecular structure for humic acid, having a variety of components including quinone, phenol, catechol and sugar moieties, is given in Scheme 1 below (source: Stevenson F. J. "*Humus Chemistry: Genesis, Composition, Reactions,*" John Wiley & Sons, New York 1994).

(Scheme 1)

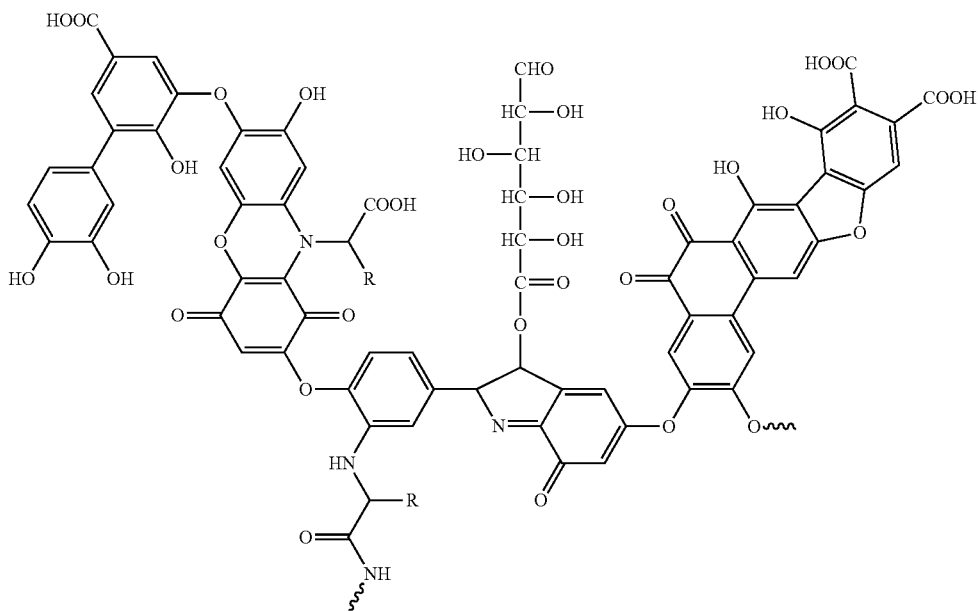

Non-aqueous solvents for humic acid include polyethylene glycol, ethylene glycol, propylene glycol, an alcohol, a sugar alcohol, a polyglycerol, a glycol ether, an amine based solvent, an amide based solvent, an alkylene carbonate, an organic acid, or an inorganic acid.

The present invention provides a process for producing a highly oriented humic acid film (with or without externally added graphene sheets) and humic acid-derived graphitic film with a thickness from 5 nm to 500 μm (more typically and preferably from 10 nm to 200 μm, even more typically from 100 nm to 100 μm, further more typically from 1 μm to 50 μm) and a physical density no less than 1.6 g/cm³ (up to 2.2 g/cm³). The process comprises:

(a) preparing a dispersion of humic acid (HA) or chemically functionalized humic acid (CHA) having HA or CHA sheets dispersed in a liquid medium, wherein the HA sheets contain an oxygen content higher than 5% by weight or the CHA sheets contain non-carbon element content higher than 5% by weight; (In certain preferred embodiments, the HA or CHA dispersion further contains graphene sheets or molecules dispersed therein and the HA-to-graphene or CHA-to-graphene ratio is from 1/100 to 100/1. These graphene sheets may be selected from pristine graphene, graphene oxide, reduced graphene oxide, graphene fluoride, graphene bromide, graphene iodide, boron-doped graphene, nitrogen-doped graphene, chemically functionalized graphene, or a combination thereof.)

(b) dispensing and depositing the HA or CHA dispersion onto a surface of a supporting substrate to form a wet layer of HA or CHA, wherein the dispensing and depositing procedure includes subjecting the dispersion to an orientation-inducing stress; (This orientation-controlling stress, typically including a shear stress, enables the HA/CHA sheets (or sheet-like molecules) and graphene sheets (if present) to get aligned along planar directions of the supporting substrate surface. Proper alignment of the HA/CHA and graphene sheets is essential to the chemical linking or merging between two or multiple HA/CHA sheets, or between HA/CHA sheets and graphene sheets during subsequent heat treatments.)

(c) partially or completely removing the liquid medium from the wet layer of HA or CHA to form a dried HA or CHA layer having hexagonal carbon planes and an inter-planar spacing $d_{002}$ of 0.4 nm to 1.3 nm as determined by X-ray diffraction; and (d) thermally treating the dried HA or CHA layer at a first heat treatment temperature higher than 80° C. for a sufficient period of time to produce the highly oriented humic acid film containing inter-connected or merged HA or CHA sheets that are substantially parallel to one another. These HA/CHA sheets typically also have been thermally reduced. This highly oriented humic acid film of reduced HA or CHA may be subjected to an additional step of compressing.

The process (with or without the step of compressing) can further comprise a step (e) of further heat-treating the humic acid film of merged and reduced HA or CHA at a second heat treatment temperature higher than the first heat treatment temperature for a sufficient period of time to produce a graphitic film having an inter-planar spacing $d_{002}$ less than 0.4 nm and an oxygen content or non-carbon element content less than 5% by weight; and (f) compressing said graphitic film to produce a highly conducting graphitic film.

In an embodiment, step (e) includes heat-treating the highly oriented humic acid film at a second heat treatment temperature higher than the first heat treatment temperature (typically >300° C.) for a length of time sufficient for decreasing an inter-plane spacing $d_{002}$ to a value of from 0.3354 nm to 0.36 nm and decreasing the oxygen content or non-carbon content to less than 0.5% by weight. In a preferred embodiment, the second (or final) heat treatment temperature includes at least a temperature selected from (A) 100-300° C., (B) 300-1,500° C., (C) 1,500-2,500° C., and/or (D) 2,500-3,200° C. Preferably, the second heat treatment temperature includes a temperature in the range of 300-1,500° C. for at least 1 hour and then a temperature in the range of 1,500-3,200° C. for at least another hour.

Typically, if both the first and second heat treatment temperatures are below 1,500° C., the highly oriented humic acid (HOHA) film still contains planar molecules that are characteristic of humic acid molecules. The highly oriented humic acid (HOHA) film contains chemically bonded and merged hexagonal carbon planes, which are HA/CHA or combined HA/CHA-graphene planes. These planes (hexagonal structured carbon atoms having a small amount of oxygen-containing group) are parallel to one another.

This HOHA film, if exposed to a heat treatment temperature (HTT) of 1,500° C. or higher for a sufficient length of time, typically no longer contains any significant amount of humic acid molecules and essentially all HA/CHA sheets/molecules have been converted to graphene- or graphene oxide-like hexagonal carbon planes that are parallel to one another. The lateral dimensions (length or width) of these planes are huge, typically several times or even orders of magnitude larger than the maximum dimensions (length/width) of the starting HA/CHA sheets. The presently invented HOHA is essentially a "giant hexagonal carbon crystal" or "giant planar graphene-like layer" having all constituent graphene-like planes being essentially parallel to one another. This is a unique and new class of material that has not been previously discovered, developed, or suggested to possibly exist.

The oriented HA/CHA layer (HOHA film with no HTT>1,500° C.) is itself a very unique and novel class of material that surprisingly has great cohesion power (self-bonding, self-polymerizing, and self-crosslinking capability). These characteristics have not been previously taught or hinted in the prior art.

Step (a) entails dispersing HA/CHA sheets or molecules in a liquid medium, which can be water or a mixture of water and an alcohol, for certain HA or CHA molecules that contain a significant amount of —OH and/or —COOH groups at the edges and/or on the planes of the HA/CHA sheets (e.g. having an oxygen content between 20% and 47% by weight, preferably between 30% and 47%).

When the volume fraction or weight fraction of HA/CHA exceeds a threshold value, the resulting dispersion is found to contain a liquid crystalline phase. Preferably, the HA/CHA suspension (dispersion) contains an initial volume fraction of HA/CHA sheets that exceeds a critical or threshold volume fraction for the formation of a liquid crystal phase prior to step (b). We have observed that such a critical volume fraction is typically equivalent to a HA/CHA weight fraction in the range of from 0.2% to 5.0% by weight of HA/CHA sheets in the dispersion. However, such a range of low HA/CHA contents is not particularly amenable to the formation of the desired thin films using a scalable process, such as casting and coating. The ability to produce thin films via casting or coating is highly advantageous and desirable since large-scaled and/or automated casting or coating systems are readily available, and the processes are known to be reliable for production of polymer thin films with consistently high quality. Therefore, we proceeded to conduct an in-depth and extensive study on the suitability for casting or coating from the dispersion containing a HA/CHA-based liquid crystalline phase. We discovered that by concentrating the dispersion to increase the HA/CHA contents from the range of 0.2% to 5.0% by weight to the range of 4% to 16% by weight of HA/CHA sheets, we obtain a dispersion that is highly suitable to large-scale production of thin graphene films. Most significantly and quite unexpectedly, the liquid crystalline phase is not only preserved, but often enhanced, making it more feasible for HA/CHA sheets to be oriented along preferred orientations during the casting or coating procedures. In particular, the HA/CHA sheets in a liquid crystal state containing 4% to 16% by weight of HA/CHA sheets have the highest tendency to get readily oriented under the influence of a shear stress created by a commonly used casting or coating process.

Thus, in step (b), the HA/CHA suspension is formed into a thin-film layer preferably under the influence of a shear stress that promotes a laminar flow. One example of such a shearing procedure is casting or coating a thin film of HA/CHA suspension using a slot-die coating machine. This procedure is similar to a layer of polymer solution being coated onto a solid substrate. The roller, "doctor's blade", or wiper creates a shear stress when the film is shaped, or when there is a relative motion between the roller/blade/wiper and the supporting substrate at a sufficiently high relative motion speed. Quite unexpectedly and significantly, such a shearing action enables the planar HA/CHA sheets to well align along, for instance, a shearing direction. Further surprisingly, such a molecular alignment state or preferred orientation is not disrupted when the liquid components in the HA/CHA suspension are subsequently removed to form a well-packed layer of highly aligned HA/CHA sheets that are at least partially dried. The dried layer has a high birefringence coefficient between an in-plane direction and the normal-to-plane direction.

The present invention includes the discovery of a facile amphiphilic self-assembly approach to fabricate HA/CHA-based thin films with desired hexagonal plane orientation. HA containing 5-46% by weight of oxygen may be considered a negatively charged amphiphilic molecule due to its combination of hydrophilic oxygen-containing functional groups and a hydrophobic basal plane. For a CHA, the functional groups can be made to be hydrophilic or hydrophobic. The successful preparation of the HA/CHA films with unique hexagonal, graphene-like plane orientations does not require complex procedures. Rather, it is achieved by tailoring HA/CHA synthesis and manipulating the liquid crystalline phase formation and deformation behaviors to enable the self-assembly of HA/CHA sheets in a liquid crystalline phase.

The HA/CHA suspension was characterized using atomic force microscopy (AFM), Raman spectroscopy, and FTIR to confirm its chemical state. Finally, the presence of lyotropic meso-morphism of HA sheets (liquid crystalline HA phase) in aqueous solution was demonstrated through cross-polarized light observation.

Two major aspects are considered to determine if a 1-D or 2-D species can form a liquid crystalline phase in a liquid medium: the aspect ratio (the length/width/diameter-to-thickness ratio) and sufficient dispersibility or solubility of this material in the liquid medium. HA or CHA sheets feature high anisotropy, with monatomic or few-atom thickness (t) and normally micrometer-scale lateral width (w). According to Onsager's theory, high aspect ratio 2D sheets can form liquid crystals in dispersions, when their volume fraction exceeds a critical value:

$$V_c \approx 4t/w \qquad (Eq. 1)$$

Given the thickness of a graphene-like plane being 0.34 nm and a width of 1 μm, the required critical volume would be $V_c \approx 4t/w = 4 \times 0.34/1,000 = 1.36 \times 10^{-3} = 0.136\%$. However, pristine graphene sheets are not soluble in water and poorly dispersible in common organic solvents (maximum volume fraction, $V_m$, ~$0.7 \times 10^{-5}$ in N-methylpyrrolidone (NMP) and ~$1.5 \times 10^{-5}$ in ortho-dichlorobenzene), owing to their strong π-π stacking attraction. Fortunately, the molecular structure of HA or CHA can be made to exhibit good dispersibility in water and polar organic solvents, such as alcohol, N,N-dimethyl formamide (DMF) and NMP, due to the numerous oxygen-containing functional groups attached to its edges. Naturally occurring HA (e.g. that from coal) is also highly soluble in non-aqueous solvents for humic acid include polyethylene glycol, ethylene glycol, propylene glycol, an alcohol, a sugar alcohol, a polyglycerol, a glycol ether, an amine based solvent, an amide based solvent, an alkylene carbonate, an organic acid, an inorganic acid, or a mixture thereof.

Although, presumably the critical volume fraction of HA/CHA can be lower than 0.2% or critical weight fraction lower than 0.3% according to theoretical prediction, we have observed that the critical weight fractions for HA/CHA sheets to form liquid crystals are significantly higher than 0.4% by weight. The most stable liquid crystals are present when the weight fraction of HA/CHA sheets is in the range of 0.6%-5.0%, which enable high stability over a wide temperature range. To study the effect of HA/CHA size on the formation of its liquid crystalline structure, HA/CHA samples were prepared using a pH-assisted selective sedimentation technique. The lateral sizes of HA/CHA sheets were assessed by dynamic light scattering (DLS) via three different measurement modes, as well as AFM.

During the investigation of HA/CHA liquid crystals we made an unexpected but highly significant discovery: The liquid crystalline phase of HA/CHA sheets in water and other solvents can be easily disrupted or destroyed with mechanical disturbances (e.g. mechanical mixing, shearing, turbulence flow, etc.). The mechanical stability of these liquid crystals can be significantly improved if the concentration of HA/CHA sheets is gradually increased to above 5% (preferably from 5% to 16% by weight) by carefully removing (e.g. vaporizing) the liquid medium without mechanically disturbing the liquid crystalline structure. We further observed that with a HA/CHA weight fraction in this range of 5-16%, HA/CHA sheets are particularly amenable to forming desired orientations during casting or coating to form thin films.

Thermodynamically, the process of amphiphilic HA/CHA self-assembly into a liquid crystalline phase is an interplay of the enthalpy change (ΔH) and entropy change (ΔS) as shown in Eq. (2):

$$\Delta G_{self-assembly} = \Delta H_{self-assembly} - T\Delta S_{self-assembly} \qquad (2)$$

Previous studies into the thermodynamic driving force for amphiphilic self-assembly into liquid crystal phases indicate that the entropic contribution plays a dominant role, while the enthalpy change is unfavorable in most cases. Onsager's theory predicts that high aspect ratio particles can form liquid crystal phases above a critical volume fraction due to a net gain in entropy as the loss of orientational entropy is compensated for by an increased translational entropy. Specifically, higher aspect ratio particles favor the formation of long-range liquid crystalline phases. Another possible reason for the HA/CHA aspect ratio effect could be the structural corrugation of HA/CHA sheets in solvent as the restoring force originated from bending the sheets is much weaker than that along the sheet. It was found that the degree of HA/CHA corrugated morphology in solvent could be further enhanced if its aspect ratio is increased. This corrugated configuration will significantly affect both the intra and intermolecular interactions of HA/CHA in suspension.

To achieve long-range ordering in an aqueous dispersion, well-exfoliated HA/CHA sheets with strong long-range electrostatic repulsion are required. Formation of liquid crystal structures out of colloidal particles typically requires a delicate balance of long-range repulsive forces, such as electrostatic forces, and short-range attractive forces, such as van der Waals forces and π-π interactions. If the long-range repulsive forces are not strong enough to overcome the short-range attractive forces, aggregation of colloidal particles or only weak formation of a lyotropic liquid crystal with small periodicity will inevitably occur. In the HA/CHA aqueous dispersion, long-range repulsive interactions are offered by the electrical double layers formed by the ionized oxygen functional groups. Although HA/CHA sheets still contain a considerable portion of hydrophobic domains, attractive π-π interactions and van der Waals forces can be effectively overcome by adjusting the long-range electrostatic repulsive forces The chemical composition of HA/CHA plays an important role in tailoring the electrostatic interaction in an aqueous or organic solvent dispersion. The increase of surface charge density will lead to an increase in the strength of the electrostatic repulsion against the attractive forces. The ratio of the aromatic and oxygenated domains can be easily tuned by the level of hexagonal carbon plane oxidation or chemical modification. The Fourier transform infrared spectroscopy under attenuated total reflectance mode (FTIR-ATR) results of the HA/CHA indicate that oxidized species (hydroxyl, epoxy, and carboxyl groups) exist on the HA/CHA surfaces. Thermogravimetric analysis (TGA) in nitrogen was used to probe the oxygen functional group density on the HA/CHA surface. For a highly oxidized HA, a mass loss of ~28% by weight is found at around 250° C. and is attributed to the decomposition of labile oxygen-containing species. Below 160° C., a mass loss of ~16 wt % is observed, corresponding to desorption of physically absorbed water. The X-ray photoelectron spectroscopy (XPS) result of HA shows that an atomic ratio of C/O is about 1.9. This suggests that the HA has a relatively high density of oxygen functional groups. In addition, we also prepared HA containing a lower density of oxygen functional groups by simply varying the thermal or chemical reduction time and temperature of heavily oxidized HA (e.g. from leonardite coal). We have observed that liquid crystals can be found with oxygen weight fractions preferentially in the range of 5%-40%, more preferably 5%-30%, and most preferably 5%-20%.

The colloidal interaction between HA sheets can be significantly influenced by the ionic strength, because the Debye screening length (κ−1) can be effectively increased by reducing the concentration of free ions surrounding HA sheets. The electrostatic repulsion of the HA liquid crystal in water could decrease as the salt concentration increases. As a result, more water is expelled from the HA interlamellar space with an accompanying reduction in d spacing. Thus, ionic impurities in the HA dispersions should be sufficiently removed, as it is a crucial factor influencing the formation of HA liquid crystal structure.

However, we have also found that introduction of some small amount of polymer (up to 10% by weight, but preferably up to 5% by weight, and most preferably up to only 2%) can help stabilize the liquid crystal phase when the HA/CHA dispersion is subjected to casting or coating operations. With proper functional groups and concentrations, the GO/CFG orientation in the resultant film could be enhanced. This also has never been taught or hinted in previous open or patent literature.

The dried HA/CHA layer may then be subjected to heat treatments. A properly programmed heat treatment procedure can involve at least two heat treatment temperatures (first temperature for a period of time and then raised to a second temperature and maintained at this second temperature for another period of time), or any other combination of at least two heat treatment temperatures (HTT) that involve an initial treatment temperature (first temperature) and a final HTT, higher than the first.

The first heat treatment temperature is for chemical linking and thermal reduction of HA/CHA and is conducted at the first temperature of >80° C. (can be up to 1,000° C., but preferably up to 700° C., and most preferably up to 300° C.). This is herein referred to as Regime 1:

Regime 1 (up to 300° C.): In this temperature range (the initial chemical linking and thermal reduction regime, chemical combination, polymerization (edge-to-edge merging), and cross-linking between adjacent HA/CHA sheets begin to occur. Multiple HA/CHA sheets are packed and chemically bonded together side by side and edge to edge to form an integrated layer of graphene oxide-like entity. In addition, a HA/CHA layer primarily undergoes thermally-induced reduction reactions, leading to a reduction of oxygen content to approximately 5% or lower. This treatment results in a reduction of inter-graphene spacing from approximately 0.8-1.2 nm (as dried) down to approximately 0.4 nm, and an increase in in-plane thermal conductivity from approximately 100 W/mK to 500 W/mK. Even with such a low temperature range, some chemical linking between HA/CHA sheets occurs. The HA/CHA sheets remain well-aligned, but the inter-graphene plane spacing remains relatively large (0.4 nm or larger). Many O-containing functional groups survive.

The highest or final HTT that the GO mass experiences may be divided into three distinct HTT regimes:

Regime 2 (300° C.-1,500° C.): In this mainly chemical linking regime, additional thermal reduction and extensive chemical combination, polymerization, and cross-linking between adjacent HA/CHA sheets occur. The chemical linking between HA/CHA and graphene sheets (e.g. GO sheets), if present, also occurs. The oxygen content is reduced to typically below 1% after chemical linking, resulting in a reduction of inter-graphene spacing to approximately 0.35 nm. This implies that some initial graphitization has already begun at such a low temperature, in stark contrast to conventional graphitizable materials (such as carbonized polyimide film) that typically require a temperature as high as 2,500° C. to initiate graphitization. This is another distinct feature of the presently invented HOHA film and its production processes. These chemical linking reactions result in an increase in in-plane thermal conductivity to 850-1,250 W/mK, and/or in-plane electrical conductivity to 3,500-4,500 S/cm.

Regime 3 (1,500-2,500° C.): In this ordering and re-graphitization regime, extensive graphitization or graphene plane merging occurs, leading to significantly improved degree of structural ordering. As a result, the oxygen content is reduced to typically 0.01% and the inter-graphene spacing to approximately 0.337 nm (achieving degree of graphitization from 1% to approximately 80%, depending upon the actual HTT and length of time). The improved degree of ordering is also reflected by an increase in in-plane thermal conductivity to >1,300-1,500 W/mK, and/or in-plane electrical conductivity to 5,000-7,000 S/cm.

Regime 4 (higher than 2,500° C.): In this re-crystallization and perfection regime, extensive movement and elimination of grain boundaries and other defects occur, resulting in the formation of nearly perfect single crystals or poly-crystalline graphene crystals with huge grains, which can be orders of magnitude larger than the original grain sizes of the starting HA/CHA sheets. The oxygen content is essentially eliminated, typically 0.01%-0.1%. The inter-graphene spacing is reduced to down to approximately 0.3354 nm (degree of graphitization from 80% to nearly 100%), corresponding to that of a perfect graphite single crystal. Quite interestingly, the graphene poly-crystal has all the graphene planes being closely packed and bonded, and all the planes are aligned along one direction, a perfect orientation. Such a perfectly oriented structure has not been produced even with the HOPG that was produced by subjecting pyrolytic graphite concurrently to an ultra-high temperature (3,400° C.) under an ultra-high pressure (300 Kg/cm$^2$). The highly oriented graphene structure can achieve such a highest degree of perfection with a significantly lower temperature and an ambient (or slightly higher compression) pressure. The structure thus obtained exhibits an in-plane thermal conductivity from 1,500 up to slightly >1,700 W/mK, and in-plane electrical conductivity to a range from 15,000 to 20,000 S/cm.

The presently invented highly oriented HA-derived structure can be obtained by heat-treating the HA/CHA layer with a temperature program that covers at least the first regime (typically requiring 1-24 hours in this temperature range), more commonly covers the first two regimes (1-10 hours preferred), still more commonly the first three regimes (preferably 0.5-5 hours in Regime 3), and most commonly all the 4 regimes (Regime 4, for 0.5 to 2 hour, may be implemented to achieve the highest conductivity).

X-ray diffraction patterns were obtained with an X-ray diffractometer equipped with CuKcv radiation. The shift and broadening of diffraction peaks were calibrated using a silicon powder standard. The degree of graphitization, g, was calculated from the X-ray pattern using the Mering's Eq, $d_{002}=0.3354\,g+0.344\,(1-g)$, where $d_{002}$ is the interlayer spacing of graphite or graphene crystal in nm. This equation is valid only when $d_{002}$ is equal or less than approximately 0.3440 nm. The HOHA having a $d_{002}$ higher than 0.3440 nm reflects the presence of oxygen-containing functional groups (such as —OH, >O, and —COOH on graphene-like plane surfaces) that act as a spacer to increase the inter-graphene spacing.

Another structural index that can be used to characterize the degree of ordering of the presently invented HOHA-derived graphitic film and conventional graphite crystals is the "mosaic spread," which is expressed by the full width at half maximum of a rocking curve (X-ray diffraction intensity) of the (002) or (004) reflection. This degree of ordering characterizes the graphite or graphene crystal size (or grain size), amounts of grain boundaries and other defects, and the degree of preferred grain orientation. A nearly perfect single crystal of graphite is characterized by having a mosaic spread value of 0.2-0.4. Most of our HOHA-derived graphitic samples have a mosaic spread value in this range of 0.2-0.4 (if produced with a heat treatment temperature (HTT) no less than 2,500° C.). However, some values are in the range of 0.4-0.7 if the HTT is between 1,500 and 2,500° C., and in the range of 0.7-1.0 if the HTT is between 300 and 1,500° C.

HA or graphene may be functionalized through various chemical routes. In one preferred embodiment, the resulting functionalized HA or functionalized graphene (collectively denoted as Gn) may broadly have the following formula(e):

$$[Gn]\text{-}R_m$$

wherein m is the number of different functional group types (typically between 1 and 5), R is selected from $SO_3H$, COOH, $NH_2$, OH, R'CHOH, CHO, CN, COCl, halide, COSH, SH, COOR', SR', $SiR'_3$, $Si(-OR'-)_yR'_3$, $Si(-O-SiR'_2-)OR'$, R", Li, $AlR'_2$, Hg—X, $TlZ_2$ and Mg—X; wherein y is an integer equal to or less than 3, R' is hydrogen, alkyl, aryl, cycloalkyl, or aralkyl, cycloaryl, or poly(alkylether), R" is fluoroalkyl, fluoroaryl, fluorocycloalkyl, fluoroaralkyl or cycloaryl, X is halide, and Z is carboxylate or trifluoroacetate.

Assuming that a polymer, such as epoxy resin, and HA or graphene sheets can be combined to make a coating composition, then the function group —$NH_2$ is of particular interest. For example, a commonly used curing agent for epoxy resin is diethylenetriamine (DETA), which can have 2 or more —$NH_2$ groups. One of the —$NH_2$ groups may be bonded to the edge or surface of a graphene sheet and the remaining un-reacted —$NH_2$ groups will be available for reacting with epoxy resin later. Such an arrangement provides a good interfacial bonding between the HA (or graphene) sheet and the resin additive.

Other useful chemical functional groups or reactive molecules may be selected from the group consisting of amidoamines, polyamides, aliphatic amines, modified aliphatic amines, cycloaliphatic amines, aromatic amines, anhydrides, ketimines, diethylenetriamine (DETA), triethylene-tetramine (TETA), tetraethylene-pentamine (TEPA), polyethylene polyamine, polyamine epoxy adduct, phenolic hardener, non-brominated curing agent, non-amine curatives, and combinations thereof. These functional groups are multi-functional, with the capability of reacting with at least two chemical species from at least two ends. Most importantly, they are capable of bonding to the edge or surface of graphene or HA using one of their ends and, during subsequent curing stage, are able to react with a resin at one or two other ends.

The above-described [Gn]-$R_m$ may be further functionalized. The resulting CFGs include compositions of the formula:

$$[Gn]\text{-}A_m,$$

where A is selected from OY, NHY, O=C—OY, P=C—NR'Y, O=C—SY, O=C—Y, —CR'1-OY, N'Y or C'Y, and Y is an appropriate functional group of a protein, a peptide, an amino acid, an enzyme, an antibody, a nucleotide, an oligonucleotide, an antigen, or an enzyme substrate, enzyme inhibitor or the transition state analog of an enzyme substrate or is selected from R'—OH, R'—$NR'_2$, R'SH, R'CHO, R'CN, R'X, R'$N^+(R')_3X^-$, $R'SiR'_3$, $R'Si(-OR'-)_yR'_{3-y}$, R'Si$(-O-SiR'_2-)OR'$, R'—R", R'—N—CO, $(C_2H_4O-)_wH$, $(-C_2H_6O-)_wH$, $(-C_2H_4O)_w-R'$, $(C_3H_6O)_w-R'$, R', and w is an integer greater than one and less than 200.

The HA and/or graphene sheets may also be functionalized to produce compositions having the formula:

$$[Gn]\text{-}[R'\text{-}A]_m$$

where m, R' and A are as defined above. The compositions of the invention also include CHAs upon which certain cyclic compounds are adsorbed. These include compositions of matter of the formula:

$$[Gn]\text{-}[X\text{-}R_a]_m$$

where a is zero or a number less than 10, X is a polynuclear aromatic, polyheteronuclear aromatic or metallopolyheteronuclear aromatic moiety and R is as defined above. Preferred cyclic compounds are planar. More preferred cyclic compounds for adsorption are porphyrins and phthalocyanines. The adsorbed cyclic compounds may be functionalized. Such compositions include compounds of the formula:

$$[Gn]\text{-}[X\text{-}A_a]_m$$

where m, a, X and A are as defined above.

The functionalized HA or graphene of the instant invention can be directly prepared by sulfonation, electrophilic addition to deoxygenated GO surfaces, or metallation. The graphene or HA sheets can be processed prior to being contacted with a functionalizing agent. Such processing may include dispersing the graphene or HA sheets in a solvent. In some instances the sheets may then be filtered and dried prior to contact. One particularly useful type of functional groups is the carboxylic acid moieties, which naturally exist on the surfaces of HAs if they are prepared from acid intercalation route discussed earlier. If an additional amount of carboxylic acid is needed, the HA sheets may be subjected to chlorate, nitric acid, or ammonium persulfate oxidation.

Carboxylic acid functionalized graphene sheets are particularly useful because they can serve as the starting point for preparing other types of functionalized graphene or HA sheets. For example, alcohols or amides can be easily linked to the acid to give stable esters or amides. If the alcohol or amine is part of a di- or poly-functional molecule, then linkage through the O— or NH— leaves the other functionalities as pendant groups. These reactions can be carried out using any of the methods developed for esterifying or aminating carboxylic acids with alcohols or amines as known in the art. Examples of these methods can be found in G. W. Anderson, et al., J. Amer. Chem. Soc. Vol. 86, pp. 1839-1842 (1964), which is hereby incorporated by reference in its entirety. Amino groups can be introduced directly onto graphitic fibrils by treating the fibrils with nitric acid and sulfuric acid to obtain nitrated fibrils, then chemically reducing the nitrated form with a reducing agent, such as sodium dithionite, to obtain amino-functionalized fibrils.

We have found that the aforementioned functional groups can be attached to HA or graphene sheet surfaces or edges for one or several of the following purposes: (a) for improved dispersion of graphene or HA in a desired liquid medium; (b) enhanced solubility of graphene or HA in a liquid medium so that a sufficient amount of graphene or HA sheets can be dispersed in this liquid that exceed the critical volume fraction for liquid crystalline phase formation; (c) enhanced film-forming capability so that thin film of otherwise discrete sheets of graphene or HA can be coated or cast; (d) improved capability of graphene or HA sheets to get oriented due to modifications to the flow behaviors; and (e) enhanced capability for graphene or HA sheets to get chemically linked and merged into larger or wider graphene planes.

EXAMPLE 1

Humic Acid and Reduced Humic Acid from Leonardite

Humic acid can be extracted from leonardite by dispersing leonardite in a basic aqueous solution (pH of 10) with a very high yield (in the range of 75%). Subsequent acidification of the solution leads to precipitation of humic acid powder. In an experiment, 3 g of leonardite was dissolved by 300 ml of double deionized water containing 1M KOH (or $NH_4OH$) solution under magnetic stirring. The pH value was adjusted to 10. The solution was then filtered to remove any big particles or any residual impurities.

The resulting humic acid dispersion, containing HC alone or with the presence of graphene oxide sheets (GO prepared in Example 3 described below), was cast onto a glass substrate to form a series of films for subsequent heat treatments.

EXAMPLE 2

Preparation of Humic Acid from Coal

In a typical procedure, 300 mg of coal was suspended in concentrated sulfuric acid (60 ml) and nitric acid (20 ml), and followed by cup sonication for 2 h. The reaction was then stirred and heated in an oil bath at 100 or 120° C. for 24 h. The solution was cooled to room temperature and poured into a beaker containing 100 ml ice, followed by a step of adding NaOH (3M) until the pH value reached 7.

In one experiment, the neutral mixture was then filtered through a 0.45-mm polytetrafluoroethylene membrane and the filtrate was dialyzed in 1,000 Da dialysis bag for 5 days. For the larger humic acid sheets, the time can be shortened to 1 to 2 h using cross-flow ultrafiltration. After purification, the solution was concentrated using rotary evaporation to obtain solid humic acid sheets. These humic sheets alone and their mixtures with graphene sheets were re-dispersed in a solvent (ethylene glycol and alcohol, separately) to obtain several dispersion samples for subsequent casting or coating.

EXAMPLE 3

Preparation of Graphene Oxide (GO) and Reduced Graphene Oxide (RGO) Sheets from Natural Graphite Powder Natural graphite from Ashbury Carbons was used as the starting material. GO was obtained by following the well-known modified Hummers method, which involved two oxidation stages. In a typical procedure, the first oxidation was achieved in the following conditions: 1100 mg of graphite was placed in a 1000 mL boiling flask. Then, 20 g of $K_2S_2O_8$, 20 g of $P_2O_5$, and 400 mL of a concentrated aqueous solution of $H_2SO_4$ (96%) were added in the flask. The mixture was heated under reflux for 6 hours and then let without disturbing for 20 hours at room temperature. Oxidized graphite was filtered and rinsed with abundant distilled water until a pH value >4.0 was reached. A wet cake-like material was recovered at the end of this first oxidation.

For the second oxidation process, the previously collected wet cake was placed in a boiling flask that contains 69 mL of a concentrated aqueous solution of $H_2SO_4$ (96%). The flask was kept in an ice bath as 9 g of $KMnO_4$ was slowly added. Care was taken to avoid overheating. The resulting mixture was stirred at 35° C. for 2 hours (the sample color turning dark green), followed by the addition of 140 mL of water. After 15 min, the reaction was halted by adding 420 mL of water and 15 mL of an aqueous solution of 30 wt % $H_2O_2$. The color of the sample at this stage turned bright yellow. To remove the metallic ions, the mixture was filtered and rinsed with a 1:10 HCl aqueous solution. The collected material was gently centrifuged at 2700 g and rinsed with deionized water. The final product was a wet cake that contained 1.4 wt % of GO, as estimated from dry extracts. Subsequently, liquid dispersions of GO platelets were obtained by lightly sonicating wet-cake materials, which were diluted in deionized water.

Figure 3A:
FIG. 3(A) A SEM image of a HA liquid crystal-derived HOGF, wherein multiple hexagonal carbon planes seamlessly merged into continuous-length graphene-like sheets or layers that can run for tens of centimeters wide or long (only a 50 μm width of a 10-cm wide HOGF being shown in this SEM image)
Figure 3A:
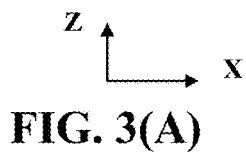
Figure 3B:
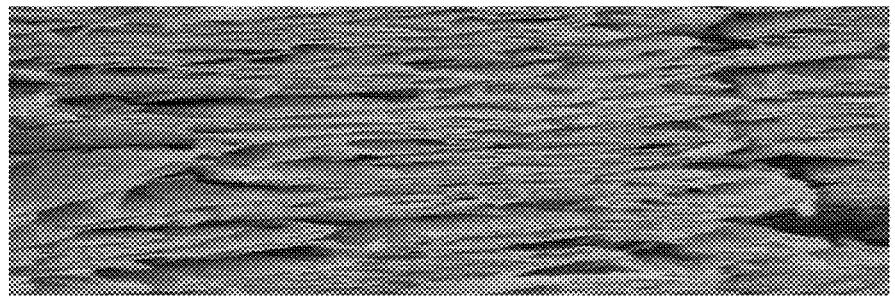
FIG. 3(B) A SEM image of a cross-section of a conventional graphene paper prepared from discrete reduced graphene oxide sheets/platelets using a paper-making process (e.g. vacuum-assisted filtration). The image shows many discrete graphene sheets being folded or interrupted (not integrated), with orientations not parallel to the film/paper surface and having many defects or imperfections.
Figure 3B:
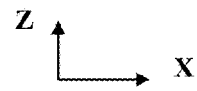
Figure 3C:
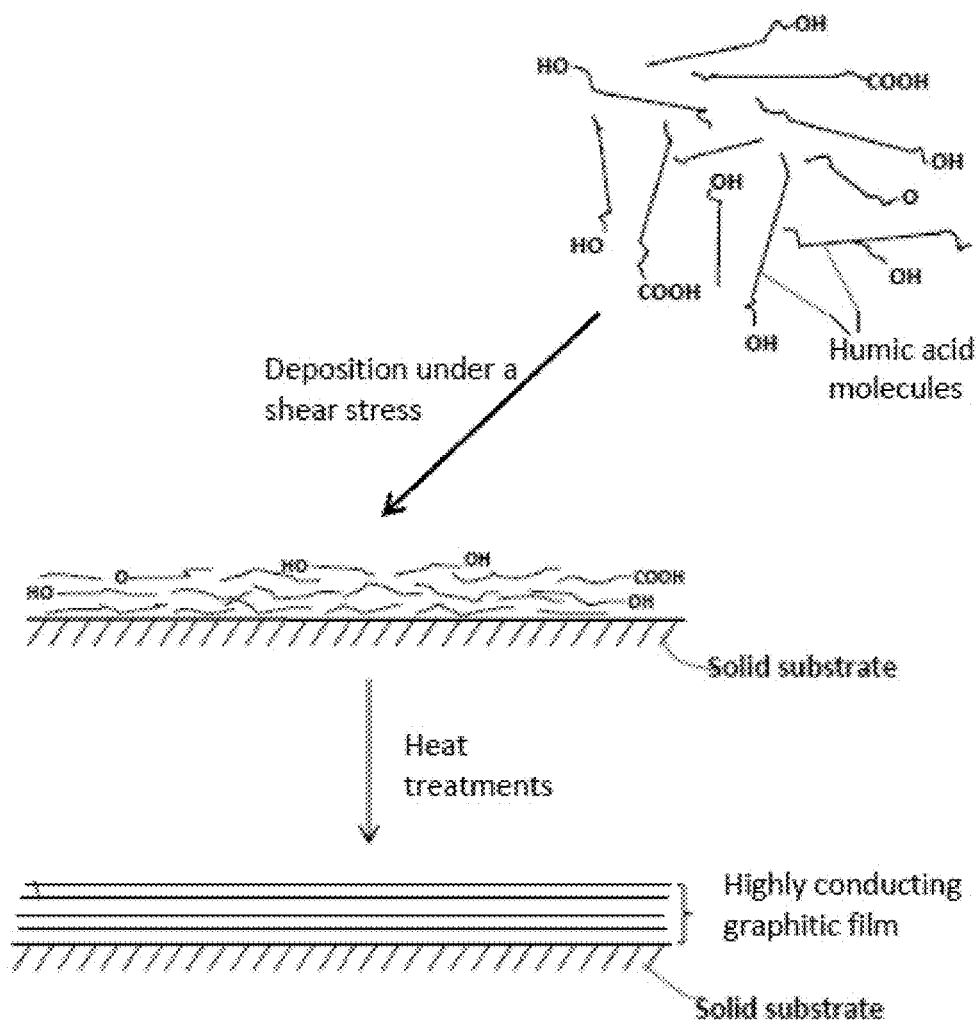
FIG. 3(C) Schematic of a film of highly oriented humic acid molecules being chemically merged together to form a highly ordered graphitic film.

On a separate basis, water suspensions containing mixtures of GO and humic acid at various GO proportions (1%, 10%, 20%, 30%, 40%, 50%, 60%, 70%, 80%, 90%, and 99%) were prepared and slot-die coated to produce thin films of various compositions, as illustrated in FIG. 3(C).

EXAMPLE 4

Preparation of Oriented Films Containing Pristine Graphene Sheets (0% Oxygen) Mixed with Humic Acid In a typical procedure, five grams of graphite flakes, ground to approximately 20 μm or less in sizes, were dispersed in 1,000 mL of deionized water (containing 0.1% by weight of a dispersing agent, Zonyl® FSO from DuPont) to obtain a suspension. An ultrasonic energy level of 85 W (Branson S450 Ultrasonicator) was used for exfoliation, separation, and size reduction of graphene sheets for a period of 15 minutes to 2 hours. The resulting graphene sheets are pristine graphene that have never been oxidized and are oxygen-free and relatively defect-free. Pristine graphene is essentially free from any non-carbon elements.

The suspension after ultrasonication contains pristine graphene sheets dispersed in water and s surfactant dissolved therein. Humic acid was then added into the suspension and the resulting mixture suspension was further ultrasonicated for 10 minutes to facilitate uniform dispersion and mixing.

EXAMPLE 5

Preparation of Highly Oriented Graphitic Films from Mixtures of Graphene Fluoride Sheets and Humic Acid Several processes have been used by us to produce GF, but only one process is herein described as an example. In a typical procedure, highly exfoliated graphite (HEG) was prepared from intercalated compound $C_2F \cdot xClF_3$. HEG was further fluorinated by vapors of chlorine trifluoride to yield fluorinated highly exfoliated graphite (FHEG). Pre-cooled Teflon reactor was filled with 20-30 mL of liquid pre-cooled $ClF_3$, the reactor was closed and cooled to liquid nitrogen temperature. Then, no more than 1 g of HEG was put in a container with holes for $ClF_3$ gas to access and situated inside the reactor. In 7 days a gray-beige product with approximate formula $C_2F$ was formed.

Subsequently, a small amount of FHEG (approximately 0.5 mg) was mixed with 20-30 mL of an organic solvent (methanol and ethanol, separately) and subjected to an ultrasound treatment (280 W) for 30 min, leading to the formation of homogeneous yellowish dispersions. Humic acid was then added to these dispersions at various HA-to-GF ratios. The dispersions were then made into thin films using comma coating. The highly oriented HA films were then heat-treated to various extents to obtain highly conducting graphitic films.

EXAMPLE 6

Preparation of HOHA Containing Nitrogenataed Graphene Sheets and Humic Acid

Graphene oxide (GO), synthesized in Example 3, was finely ground with different proportions of urea and the pelletized mixture heated in a microwave reactor (900 W) for 30 s. The product was washed several times with deionized water and vacuum dried. In this method graphene oxide gets simultaneously reduced and doped with nitrogen. The products obtained with graphene:urea mass ratios of 1:0.5, 1:1 and 1:2 are designated as NGO-1, NGO-2 and NGO-3 respectively and the nitrogen contents of these samples were 14.7, 18.2 and 17.5 wt % respectively as found by elemental analysis. These nitrogenataed graphene sheets remain dispersible in water. Various amounts of HA, having oxygen contents of 20.5% to 45%, were added into the suspensions. The resulting suspension of nitrogenated graphene-HA dispersions were then coated onto a plastic film substrate to form wet films, which were then dried and peeled off from the plastic film and subjected to heat treatments at various heat treatment temperatures, from 80 to 2,900° C. to obtain highly oriented humic acid (HOHA) films (if final HTT<1,500° C.) or highly ordered and conducting graphitic films (if 1,500° C. or higher).

EXAMPLE 7

Preparation of Nematic Liquid Crystals from Humic Acid Sheets

Humic acid aqueous dispersions were prepared by dispersing HA sheets in deionized water by mild sonication. Any acidic or ionic impurities in the dispersions were removed by dialysis, which is a crucial step for liquid-crystal formation.

A low-concentration dispersion (typically 0.05-0.6 wt. %) immobilized for a sufficiently long time (usually more than 2 weeks) macroscopically phase-separated into two phases. While the low-density top phase was optically isotropic, the high-density bottom phase demonstrated prominent optical birefringence between two crossed polarizers. A typical nematic schlieren texture consisting of dark and bright brushes was observed in the bottom phase. This is biphasic behavior, where an isotropic phase and nematic phase coexist. The compositional range for the biphase was significantly broad because of the large polydispersity of the HA molecules. It may be noted that ionic strength and pH values significantly influence the stability of HA liquid crystals. The electrostatic repulsion from the dissociated surface functional groups such as carboxylate plays a crucial role in the stability of HA liquid crystals. Thus, reducing repulsive interaction by increasing ionic strength or lowering pH values increased the coagulation of HA sheets.

We observed that substantially all HA sheets form a liquid crystal phase when HA sheets occupy a weight fraction of 1.1%, and the liquid crystals can be preserved by gradually increasing the concentration of HA to the range of from 6% to 16%. The prepared humic acid dispersion exhibited an inhomogeneous, chocolate-milk-like appearance to the naked eye. This milky appearance can be mistaken for aggregation or precipitation of the graphene oxide but, in fact, it is a nematic liquid crystal.

By dispensing and coating the HA suspension on a polyethylene terephthalate (PET) film in a slurry coater and removing the liquid medium from the coated film we obtained a thin film of dried HA. Each film was then subjected to different heat treatments, which typically include a chemical linking and thermal reduction treatment at a first temperature of 80° C. to 300° C. for 1-10 hours, and at a second temperature of 1,500° C.-2,850° C. for 0.5-5 hours. With these heat treatments, also under a compressive stress, the HOHA film was transformed into a highly conducting graphitic film (HOGF).

The internal structures (crystal structure and orientation) of several dried HA layers (HOHA films), and the HOGF at different stages of heat treatments were investigated. X-ray diffraction curves of a layer of dried HOHA prior to a heat treatment, a HOHA film thermally reduced at 150° C. for 5 hours, and the resultant HOGF were obtained. The peak at approximately $2\theta=12°$ of the dried HOHA layer corresponds to an inter-graphene spacing ($d_{002}$) of approximately 0.75 nm. With some heat treatment at 150° C., the dried film exhibits the formation of a hump centered at 22°, indicating that it has begun the process of decreasing the inter-planar spacing, indicating the beginning of chemical linking and ordering processes. With a heat treatment temperature of 2,500° C. for one hour, the $d_{002}$ spacing has decreased to approximately 0.336, close to 0.3354 nm of a graphite single crystal.

With a heat treatment temperature of 2,750° C. for one hour, the $d_{002}$ spacing is decreased to approximately to 0.3354 nm, identical to that of a graphite single crystal. In addition, a second diffraction peak with a high intensity appears at $2\theta=55°$ corresponding to X-ray diffraction from (004) plane. The (004) peak intensity relative to the (002) intensity on the same diffraction curve, or the I(004)/I(002) ratio, is a good indication of the degree of crystal perfection and preferred orientation of graphene planes. It is well-known in the art that the (004) peak is either non-existing or relatively weak, with the I(004)/I(002) ratio <0.1, for all conventional graphitic materials heat treated at a temperature lower than 2,800° C. The I(004)/I(002) ratio for the graphitic materials heat treated at 3,000-3,250° C. (e.g., highly oriented pyrolytic graphite, HOPG) is in the range of 0.2-0.5. In contrast, a HOGF prepared from the HA liquid crystal-based film with a final HTT of 2,750° C. for one hour exhibits a I(004)/I(002) ratio of 0.77 and a Mosaic spread value of 0.21, indicating a practically perfect graphene single crystal with an exceptionally high degree of preferred orientation.

The "mosaic spread" value is obtained from the full width at half maximum of the (002) reflection in an X-ray diffraction intensity curve. This index for the degree of ordering characterizes the graphite or graphene crystal size (or grain size), amounts of grain boundaries and other defects, and the degree of preferred grain orientation. A nearly perfect single crystal of graphite is characterized by having a mosaic spread value of 0.2-0.4. Most of our HA-derived HOGF have a mosaic spread value in this range of 0.2-0.4 when produced using a final heat treatment temperature no less than 2,500° C.

It may be noted that the I(004)/I(002) ratio for all tens of flexible graphite foil compacts investigated are all <<0.05, practically non-existing in most cases. The I(004)/I(002) ratio for all graphene paper/membrane samples prepared with a vacuum-assisted filtration method is <0.1 even after a heat treatment at 3,000° C. for 2 hours. These observations have further confirmed the notion that the presently invented HOHA film is a new and distinct class of material that is fundamentally different from any pyrolytic graphite (PG), flexible graphite (FG), and paper/film/membrane of conventional graphene/GO/RGO sheets/platelets (NGPs).

Figure 5A:
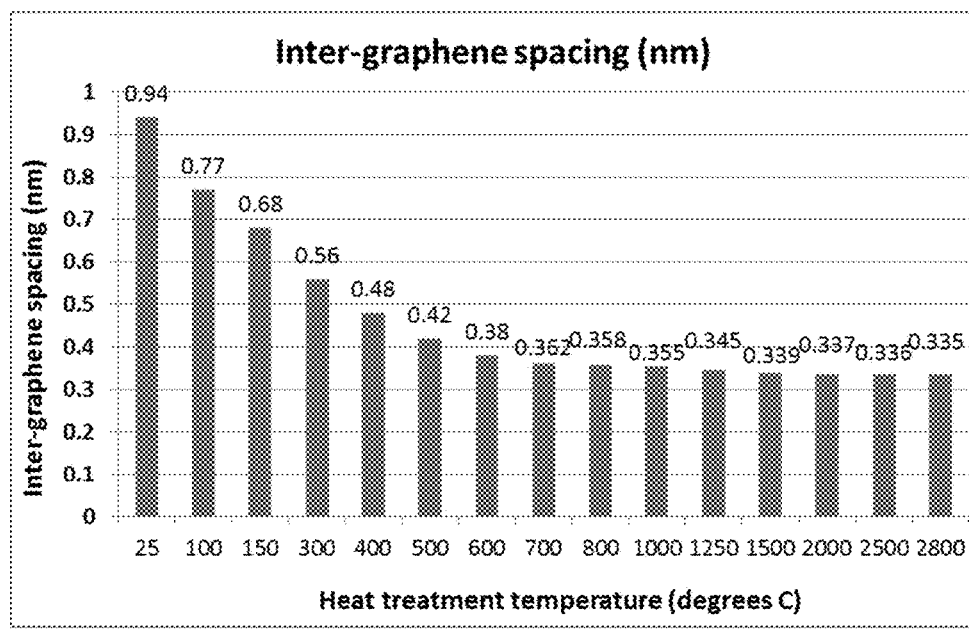
FIG. 5(A) Inter-graphene plane spacing in HA-derived HOGF measured by X-ray diffraction.
Figure 5B:
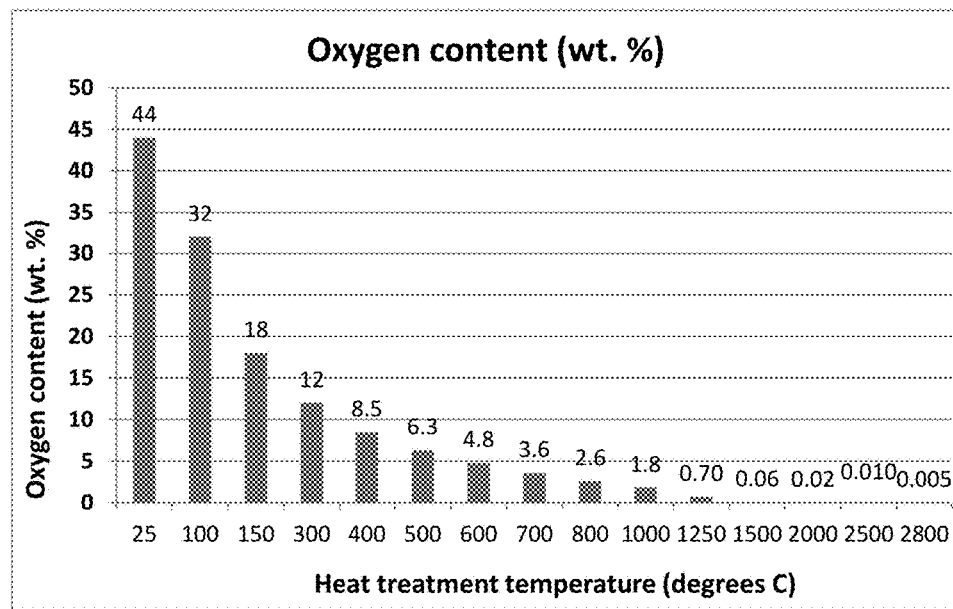
FIG. 5(B) The oxygen content in the HA-derived HOGF.
Figure 5C:
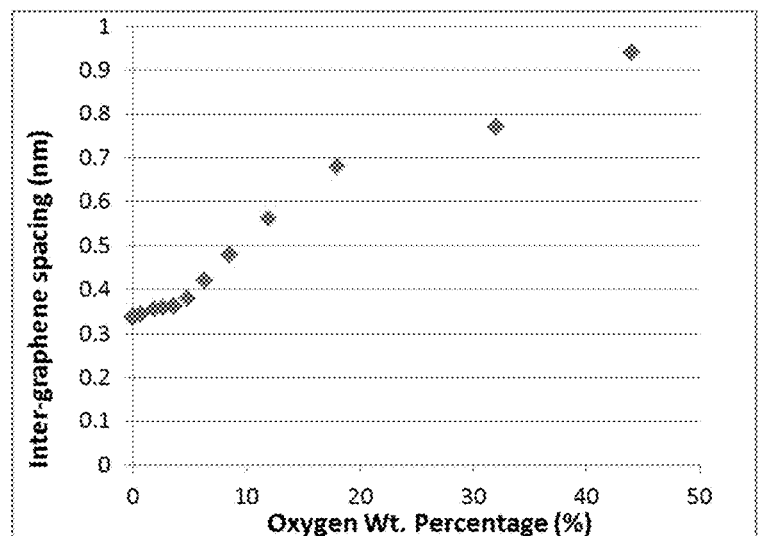
FIG. 5(C) The correlation between inter-graphene spacing and the oxygen content.
Figure 5D:
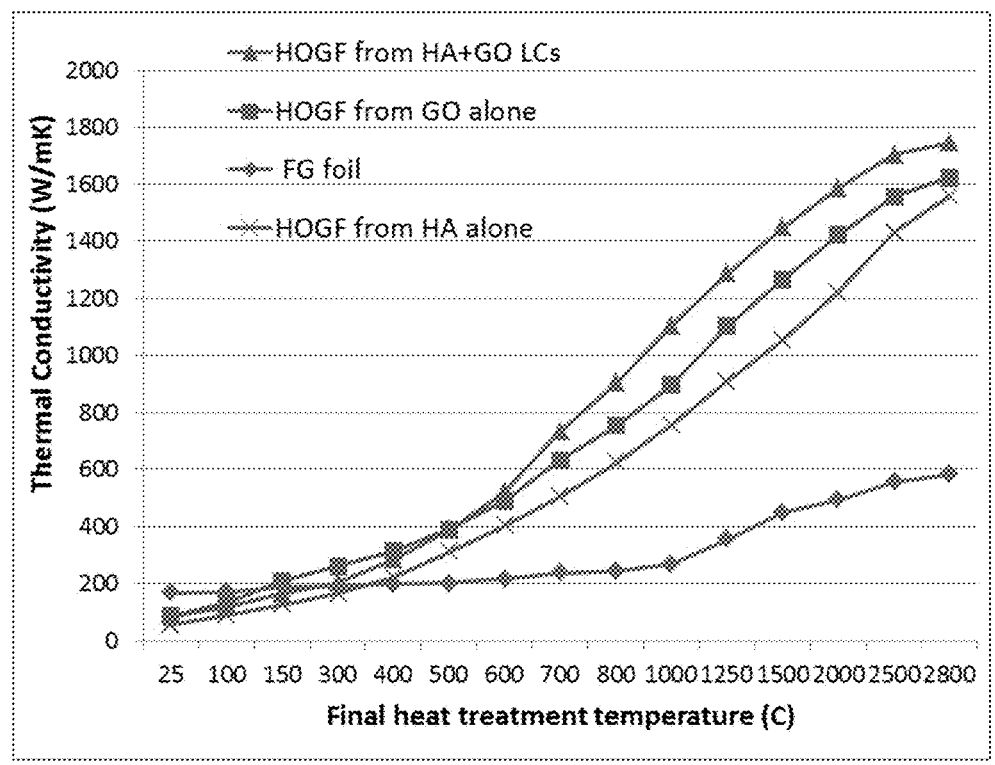
FIG. 5(D) Thermal conductivity values of the (HA+GO)-derived HOGF, GO-derived HOGF, HA-derived HOGF, and FG foil plotted as a function of the final heat treatment temperature.

The inter-graphene spacing values of both the HA liquid crystal suspension-derived HOGF samples obtained by heat treating at various temperatures over a wide temperature range are summarized in FIG. 5(A). Corresponding oxygen content values are shown in FIG. 5(B). In order to show the correlation between the inter-graphene spacing and the oxygen content, the data in FIGS. 5(A) and 5(B) are re-plotted in FIG. 5(C). A close scrutiny of FIG. 5(A)-(C) indicate that there are four HTT ranges (100-300° C.; 300-1,500° C.; 1,500-2,000° C., and >2,000° C.) that lead to four respective oxygen content ranges and inter-graphene spacing ranges. The thermal conductivity of the HA liquid crystal-derived HOGF specimens and the corresponding sample of flexible graphite (FG) foil sheets, also plotted as a function of the same final heat treatment temperature range, is summarized in FIG. 5(D). All these samples have comparable thickness values.

It is of significance to point out that a heat treatment temperature as low as 500° C. is sufficient to bring the average inter-planar spacing to below 0.4 nm, getting closer and closer to that of natural graphite or that of a graphite single crystal. The beauty of this approach is the notion that this HA liquid crystal suspension strategy has enabled us to re-organize, re-orient, and chemically merge the planar HA sheets into a unified structure with all the graphene-like planes now being larger in lateral dimensions (significantly larger than the length and width of the hexagonal carbon planes in the original HA molecules) and essentially parallel to one another. This has given rise to a thermal conductivity already 300-400 W/mK (with a HTT of 500° C.) and >623 W/mk (from HA only) or >900 W/mk (from mixture of HA+GO) with a HTT of 700° C., which is more than 3- to 4-fold greater than the value (200 W/mK) of the corresponding flexible graphite foil. Furthermore, the tensile strength of the HOGF samples can reach 90-125 MPa (FIG. 7(A)).

Figure 4A:
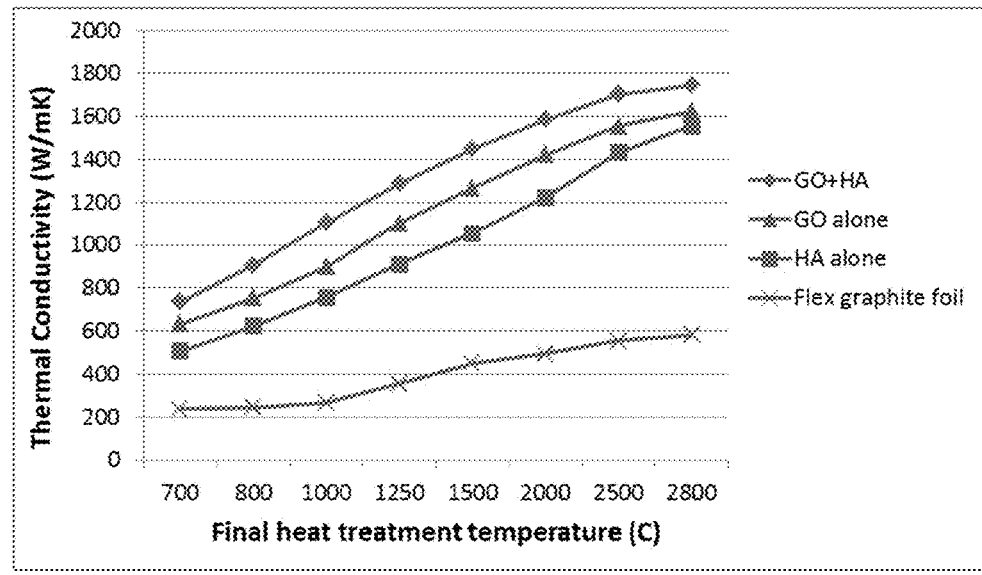
FIG. 4(A) Thermal conductivity values of the (HA+GO)-derived HOGF, GO-derived HOGF, HA-derived HOGF, and FG foil plotted as a function of the final heat treatment temperature.

With a HTT as low as 1,000° C., the resulting highly oriented HA film exhibits a thermal conductivity of 756 W/mK (from HA alone) and 1,105 W/mK (from a HA-GO mixture), respectively. This is in stark contrast to the observed 268 W/mK of the flexible graphite foil with an identical heat treatment temperature. As a matter of fact, no matter how high the HTT is (e.g. even as high as 2,800° C.), the flexible graphite foil only shows a thermal conductivity lower than 600 W/mK. At a HTT of 2,800° C., the presently invented HOGF layer delivers a thermal conductivity of 1,745 W/mK for a layer derived from a mixture of HA and GO (FIG. 4(A) and FIG. 5(D)). It may be further noted that, as indicated in FIG. 4(A), the thermal conductivity values of HA/GO mixture-derived graphitic films are consistently higher than those of corresponding graphitic films derived from graphene oxide. This surprising effect is further discussed in Example 8.

Scanning electron microscopy (SEM), transmission electron microscopy (TEM) pictures of lattice imaging of the graphene layer, as well as selected-area electron diffraction (SAD), bright field (BF), and dark-field (DF) images were also conducted to characterize the structure of unitary graphene materials. For measurement of cross-sectional views of the film, the sample was buried in a polymer matrix, sliced using an ultra-microtome, and etched with Ar plasma.

Figure 2:
FIG. 2 An SEM image of a cross-section of a flexible graphite foil, showing many graphite flakes with orientations not parallel to the flexible graphite foil surface plane and also showing many defects, kinked or folded flakes.

A close scrutiny and comparison of FIG. 2, FIG. 3(A), and FIG. 3(B) indicates that the graphene-like layers in a HOGF are substantially oriented parallel to one another; but this is not the case for flexible graphite foil and graphene oxide paper. The inclination angles between two identifiable layers in the highly conducting graphitic film are generally less than 10 degrees and mostly less than 5 degrees. In contrast, there are so many folded graphite flakes, kinks, and mis-orientations in flexible graphite that many of the angles between two graphite flakes are greater than 10 degrees, some as high as 45 degrees (FIG. 2). Although not nearly as bad, the mis-orientations between graphene platelets in NGP paper (FIG. 3(B)) are also high and there are many gaps between platelets. The HOGF entity is essentially gap-free.

FIG. 4 (A) shows the thermal conductivity values of the HA/GO-derived film, GO-derived film, HA suspension-derived HOGF, and FG foil, respectively, all plotted as a function of the final HTT. These data have clearly demonstrated the superiority of the presently invented HA/GO-derived HOGF structures in terms of the achievable thermal conductivity at a given heat treatment temperature.

1) The HA/GO liquid crystal suspension-derived HOGF appears to be superior to the GO gel-derived HOGF in thermal conductivity at comparable final heat treatment temperatures. The heavy oxidation of graphene sheets in GO gel might have resulted in high defect populations on graphene surfaces even after thermal reduction and re-graphitization. However, the presence of HA molecules seem to be capable of helping to heal the defects or bridging the gaps between GO sheets.
2) Although the highly oriented films derived from HA alone exhibit thermal conductivity values slightly lower than those derived from GO alone, the HA, as a material, is naturally abundant and it does not require the use of undesirable chemicals to produce HA. HA is one order of magnitude less expensive than natural graphite (a raw material for GO) and 2-4 orders of magnitude less expensive than GO.
3) For comparison, we have also obtained conventional highly oriented pyrolytic graphite (HOPG) samples from the polyimide (PI) carbonization route. The polyimide films were carbonized at 500° C. for 1 hour, at 1,000° C. for 3 hours, and at 1,500° C. for 12 hours in an inert atmosphere. The carbonized PI films were then graphitized at a temperature in the range of 2,500-3,000° C., under a compressive force, for 1 to 5 hours to form a conventional HOPG structure.

Figure 4B:
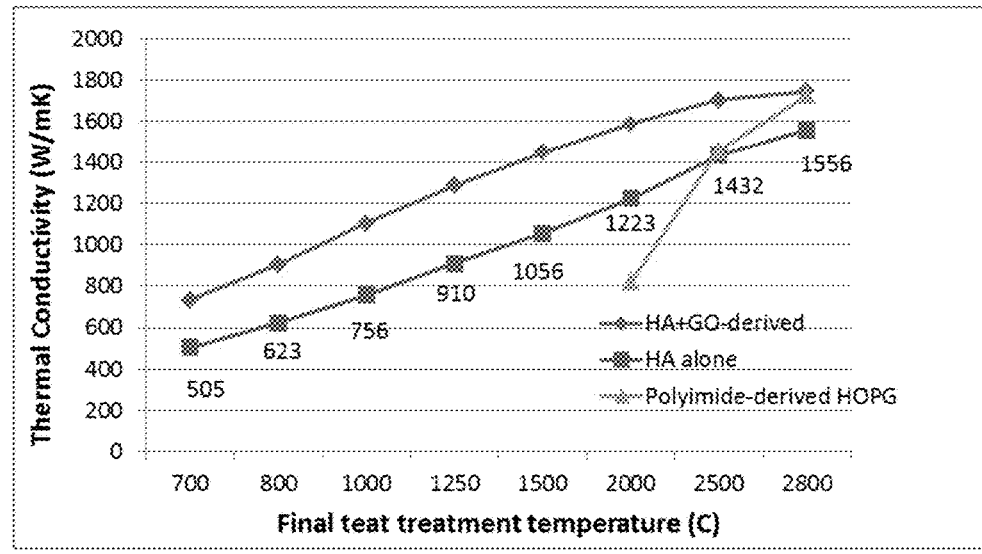
FIG. 4(B) Thermal conductivity values of the (HA+GO)-derived HOGF, HA-derived HOGF, and polyimide-derived HOPG, all plotted as a function of the final HTT.

FIG. 4(B) shows the thermal conductivity values of the HA/GO suspension-derived HOGF, the HA suspension-derived HOGF, and the polyimide-derived HOPG, all plotted as a function of the final graphitization temperature. These data show that the conventional HOPG, produced by using the carbonized polyimide (PI) route, exhibits a consistently lower thermal conductivity as compared to the HA/GO-derived HOGF, given the same HTT for the same length of heat treatment time. For instance, the HOPG from PI exhibits a thermal conductivity of 820 W/mK after a graphitization treatment at 2,000° C. for 1 hour. At the same final graphitization temperature, the HA/GO-derived HOGF exhibits a thermal conductivity value of 1,586 W/mK. It may be noted that PI is also orders of magnitude more expensive than HA and the production of PI involves the use of several environmentally undesirable organic solvents.

4) These observations have demonstrated a clear and significant advantage of using the HA/GO or HA suspension approach to producing HOGF materials versus the conventional PG approach to producing oriented graphite crystals. As a matter of fact, no matter how long the graphitization time is for the HOPG, the thermal conductivity is always lower than that of a HA/GO liquid crystal-derived HOGF. It is also surprising to discover that humic acid molecules are capable of chemically linking with one another to form strong and highly conducting graphitic films. It is clear that, the highly oriented HA film (including highly oriented HA/GO film), and the subsequently heat-treated versions are fundamentally different and patently distinct from the flexible graphite (FG) foil, graphene/GO/RGO paper/membrane, and pyrolytic graphite (PG) in terms of chemical composition, crystal and defect structure, crystal orientation, morphology, process of production, and properties.

Figure 4C:
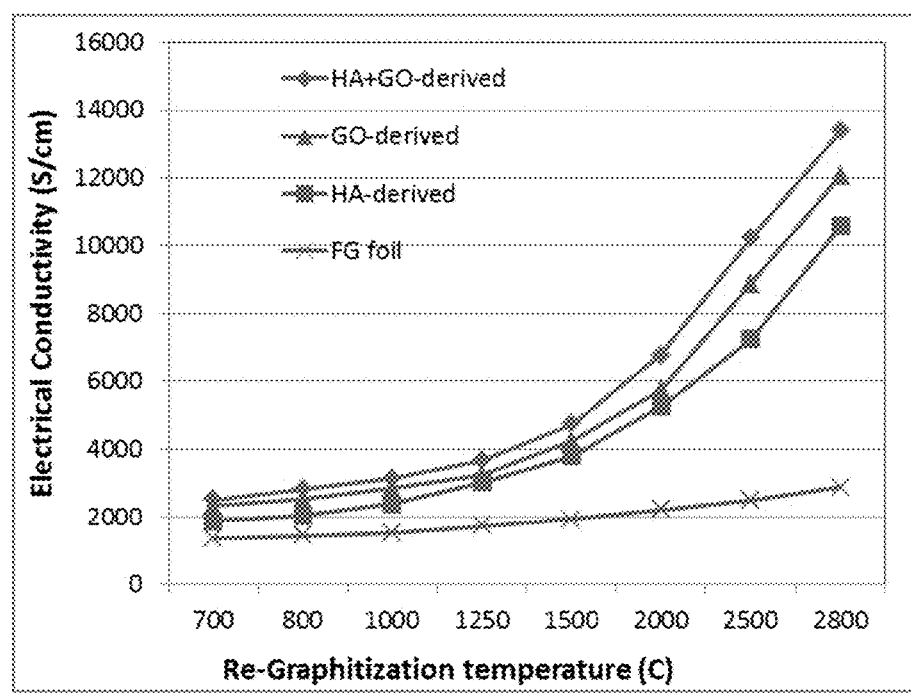
FIG. 4(C) Electric conductivity values of the (HA+GO)-derived HOGF, GO-derived HOGF, HA-derived HOGF, and FG foil plotted as a function of the final heat treatment temperature.

5) The above conclusion is further supported by the data in FIG. 4(C) showing the electric conductivity values of the HA/GO suspension-derived and HA suspension-derived HOGF HOGF are far superior to those of the FG foil sheets over the entire range of final HTTs investigated.

EXAMPLE 8

Figure 6:
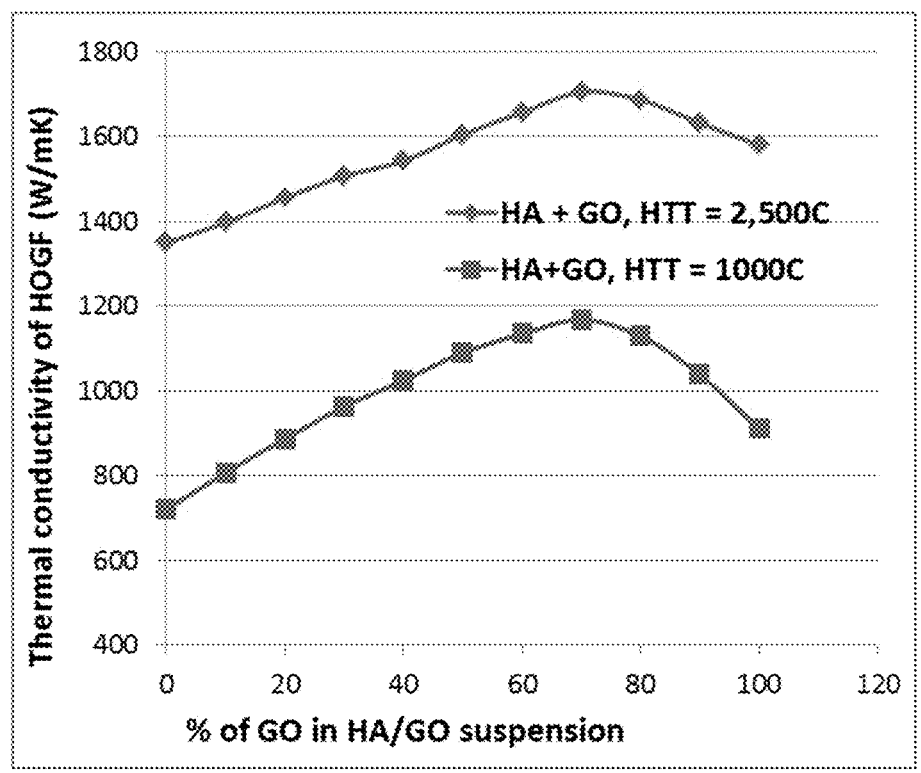
FIG. 6 Thermal conductivity of HOGF samples plotted as a function of the proportion of GO sheets in a HA/GO suspension.

The Effect of Graphene Addition on the Properties of HA-Based HOHA and Highly Oriented Graphitic Film Films Various amounts of graphene oxide (GO) sheets were added to HA suspensions to obtain mixture suspensions wherein HA and GO sheets are dispersed in a liquid medium. The same procedure as described above was then followed to produce HOGF samples of various GO proportions. The thermal conductivity data of these samples are summarized in FIG. 6, which indicate that the thermal conductivity values of the HOGF produced from the HA-GO mixtures are higher than those of the HOGF films produced from single-component alone.

Further surprisingly, there are synergistic effects that can be observed when both the HA sheets and GO sheets co-exist in proper proportions. It seems that HA can help GO sheets (known to be highly defected) heal from their otherwise defected structure. It is also possible that HA molecules, being significantly smaller in size than GO sheets/molecules, can fill in the gaps between GO molecules and react therewith to bridge the gaps. These two factors likely lead to the significantly improved conductivity.

EXAMPLES 9

Tensile Strength of Various Graphene Oxide-Derived HOHA Films

Figure 7A:
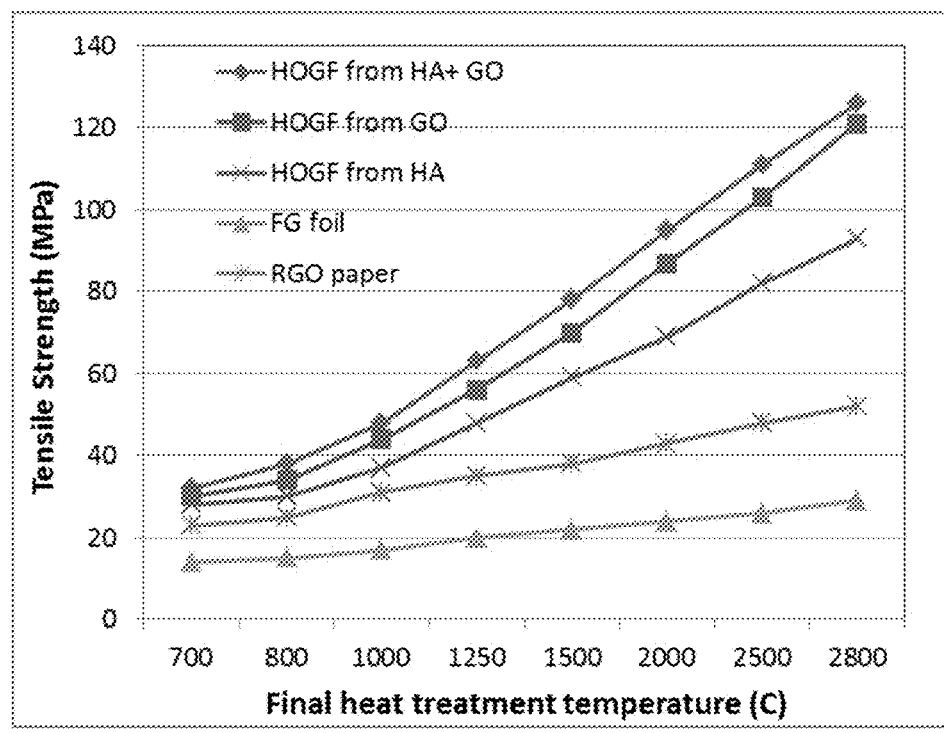
FIG. 7(A) Tensile strength values of (HA+GO)-derived HOGF, GO-derived HOGF, HA-derived HOGF, flexible graphite foil, and reduced graphene oxide paper, all plotted as a function of the final heat treatment temperature.
Figure 7B:
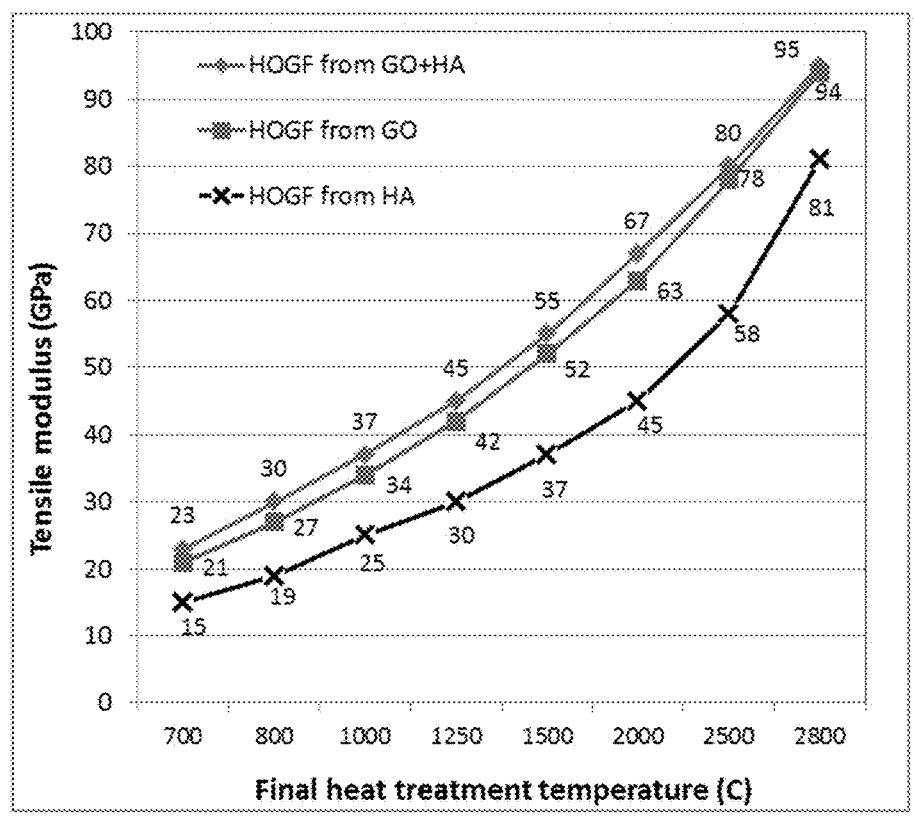
FIG. 7(B) Tensile modulus of the (HA+GO)-derived HOGF, GO-derived HOGF, and HA-derived HOGF, plotted as a function of the final heat treatment temperature.

A series of HA/GO dispersion-derived HOGF, GO dispersion-derived HOGF, and HA-derived HOGF films were prepared by using a comparable final heat treatment temperature for all materials. A universal testing machine was used to determine the tensile properties of these materials. The tensile strength and modulus of these various samples prepared over a range of heat treatment temperatures are shown in FIG. 7(A) and FIG. 7(B), respectively. For comparison, some tensile strength data of RGO paper and flexible graphite foil are also summarized in FIG. 7(A).

These data have demonstrated that the tensile strength of the graphite foil-derived sheets increases slightly with the final heat treatment temperature (from 14 to 29 MPa) and that of the GO paper (compressed/heated sheets of GO paper) increases from 23 to 52 MPa when the final heat treatment temperature increases from 700 to 2,800° C. In contrast, the tensile strength of the HA-derived HOGF increases significantly from 28 to 93 MPa over the same range of heat treatment temperatures. Most dramatically, the tensile strength of the HA/GO suspension-derived HOGF increases significantly from 32 to 126 MPa. This result is quite striking and further reflects the notion that the HA/GO and HA dispersion contains highly oriented/aligned, chemically active HA/GO and HA sheets/molecules that are capable of chemical linking and merging with one another during the heat treatment, while the graphene platelets in the conventional GO paper and the graphite flakes in the FG foil are essentially dead platelets. The HA or HA/GO-based highly oriented films and the subsequently produced graphitic films is a new class of material by itself.

As a point of reference, the film, obtained by simply spraying HA-solvent solution onto a glass surface and drying the solvent, does not have any strength (it is so fragile that you can break the film by simply touch the film with a finger). After heat treating at a temperature >100° C., this film became fragmented (broken into a huge number of pieces). In contrast, the highly oriented HA film (wherein all HA molecules or sheets are highly oriented and packed together), upon heat treatment at 150° C. for one hour, became a film of good structural integrity, having a tensile strength >24 MPa.

EXAMPLE 10

Synthesis of Polyacrylonitrile-Grafted HA (HA-g-PAN)

Acrylonitrile (AN) was dried over calcium chloride for 48 h, distilled under reduced pressure, and stored at −20° C. 2,2'Azobis(2-methylpropionitrile) (AIBN) and potassium persulfate ($K_2S_2O_8$) were employed after twice recrystallization.

To study an example of chemically functionalized HA, PAN was grafted onto HA sheets via the in situ free radical polymerization procedure. Typically, 100 mg of HA and 80 mL of dimethylformamide (DMF) were added to a 150 mL round-bottom flask, and a well-dispersed solution was obtained by sonicating in a 40 kHz sonic bath for 10 min. Followed by addition of 10.6 g of AN (200 mmol) and 82 mg of initiator of AIBN (0.5 mmol), the solution was purged with nitrogen for 40 min and then immersed in an oil bath at 65° C. After reacting for 48 h under $N_2$ protection and stirring, the reaction was terminated by exposure to air. The resultant mixture was precipitated in methanol, and the resulting gray precipitate was collected and re-dissolved in 200 mL of DMF. The solution was then centrifuged at the speed of 15 000 rpm (23,300 G) for 0.5-1 h to remove free polymers that were not covalently attached to HA. The resultant cream-like fluid was thoroughly washed with DMF for eight times until the upper layer appeared colorless. Then the resulting black colloidal product of HA-g-PAN was dispersed in 50 mL of DMF ready for use.

The polymer-modified HA sheets were found to undergo transition from an isotropic phase to a liquid crystalline phase at a higher threshold volume fraction ($V_c$), which seems to be a little disadvantage, but since coating or casting was conducted with a dispersion of significantly higher concentration (e.g. >3% by weight far exceeding $V_c$), this high $V_c$ is not a concern. However, this polymer component has made it easier to form thin films with good mechanical integrity and improved ease of handling, which are highly desirable features. A HA-g-PAN dispersion was cast to produce a wet film, which was dried and thermally treated, at 300° C. for 5 hours, 1,000° C. for 3 hours, and then 2,500° C. for 2 hours. The density of HA-g-PAN liquid crystal-derived film is 2.13 g/cm³, exhibiting a thermal conductivity of 1,566 W/mk.

For comparison, the paper of HA-g-PAN was prepared by vacuum-assisted filtration of DMF dispersion with concentration of 5 mg/mL, followed by drying at 50° C. in vacuum for 12 h. The paper sheet was compressed and then subjected to the same thermal treatments. The density of HA-g-PAN paper-derived film is 1.70 g/cm³, exhibiting a thermal conductivity of 805 W/mk.

In conclusion, we have successfully developed an absolutely new, novel, unexpected, and patently distinct class of highly conducting and high-strength material and processes of production: highly oriented humic acid film and highly conductive graphitic film (HOGF) derived therefrom. The chemical composition (oxygen content), structure (crystal perfection, grain size, defect population, etc), crystal orientation, morphology, process of production, and properties of this new class of materials are fundamentally different and patently distinct from flexible graphite foil, polymer-derived pyrolytic graphite, CVD-derived HOPG, graphene-based thermal film, and catalytic CVD graphene thin film. The thermal conductivity, electrical conductivity, elastic modulus, and tensile strength exhibited by the presently invented materials are much higher than what prior art flexible graphite sheets, paper of discrete graphene/GO/RGO platelets, or other graphitic materials could possibly achieve. These HOGF materials have the best combination of excellent electrical conductivity, thermal conductivity, mechanical strength, and stiffness (modulus). These HOGF materials can be used in a wide variety of thermal management applications. For instance, due to its exceptional thermal conductivity, a HOGF structure can be part of a thermal management device, such as a heat dissipation film used in a smart phone, tablet computer, flat-panel TV display, or other microelectronic or communications device.

We claim:

1. A process for producing a highly oriented humic acid film with a thickness from 5 nm to 500 μm and a physical density no less than 1.3 g/cm³, said process comprising:
    (a) preparing a dispersion of humic acid (HA) or chemically functionalized humic acid (CHA) sheets dispersed in a liquid medium, wherein said HA sheets contain an oxygen content higher than 5% by weight or said CHA sheets contain non-carbon element content higher than 5% by weight;
    (b) dispensing and depositing said HA or CHA dispersion onto a surface of a supporting substrate to form a wet layer of HA or CHA, wherein said dispensing and depositing procedure includes subjecting said dispersion to an orientation-inducing stress;
    (c) partially or completely removing said liquid medium from the wet layer of HA or CHA to form a dried HA or CHA layer having hexagonal carbon planes and an inter-planar spacing $d_{002}$ of 0.4 nm to 1.3 nm as determined by X-ray diffraction; and
    (d) heat-treating said dried HA or CHA layer at a first heat treatment temperature higher than 80° C. for a sufficient period of time to produce said highly oriented humic acid film containing inter-connected, merged or thermally reduced HA or CHA sheets that are substantially parallel to each other.

2. The process of claim 1, further comprising a step (e) of further heat-treating said humic acid film of merged or reduced HA or CHA at a second heat treatment temperature higher than the first heat treatment temperature for a sufficient period of time to produce a graphitic film having an inter-planar spacing $d_{002}$ less than 0.4 nm and an oxygen content or non-carbon element content less than 5% by weight; and (f) compressing said graphitic film to produce a highly conducting graphitic film having a physical density no less than 1.6 g/cm³.

3. The process of claim 2, wherein said second heat treatment temperature is higher than 1,500° C. for a length of time sufficient for decreasing an inter-plane spacing $d_{002}$ to a value less than 0.36 nm and decreasing the oxygen content or non-carbon element content to less than 0.1% by weight.

4. The process of claim 2, wherein said second heat treatment temperature is from 1,500° C. to 3,200° C.

5. The process of claim 2, wherein said first and/or second heat treatment temperature contains a temperature greater than 2,100° C. and the highly conducting graphitic film has an oxygen content no greater than 0.1%, an inter-graphene spacing less than 0.340 nm, a mosaic spread value no greater than 0.7, a thermal conductivity of at least 1,300 W/mK, and/or an electrical conductivity no less than 8,000 S/cm.

6. The process of claim 2, wherein said second heat treatment temperature contains a temperature no less than 2,500° C. and the highly conducting graphitic film has an inter-graphene spacing less than 0.336 nm, a mosaic spread value no greater than 0.4, a thermal conductivity greater than 1,600 W/mK, and/or an electrical conductivity greater than 10,000 S/cm.

7. The process of claim 2, wherein said highly conducting graphitic film is a poly-crystal graphene structure having a preferred crystalline orientation as determined by said X-ray diffraction method.

8. The process of claim 2, wherein said highly oriented graphitic film has an electrical conductivity greater than 5,000 S/cm, a thermal conductivity greater than 800 W/mK, a physical density greater than 1.9 g/cm³, a tensile strength greater than 80 MPa, and/or an elastic modulus greater than 60 GPa.

9. The process of claim 2, wherein said highly oriented graphitic film has an electrical conductivity greater than 8,000 S/cm, a thermal conductivity greater than 1,200 W/mK, a physical density greater than 2.0 g/cm³, a tensile strength greater than 100 MPa, and/or an elastic modulus greater than 80 GPa.

10. The process of claim 2, wherein said highly oriented graphitic film has an electrical conductivity greater than 12,000 S/cm, a thermal conductivity greater than 1,500 W/mK, a physical density greater than 2.1 g/cm³, a tensile strength greater than 120 MPa, and/or an elastic modulus greater than 120 GPa.

11. The process of claim 1, further comprising a step of compressing said humic acid film of merged or reduced HA or CHA after said step (d).

12. The process of claim 1, wherein said HA or CHA dispersion further contains graphene sheets or molecules dispersed therein and said HA-to-graphene or CHA-to-graphene ratio is from 1/100 to 100/1 and said graphene is selected from pristine graphene, graphene oxide, reduced graphene oxide, graphene fluoride, graphene bromide, graphene iodide, boron-doped graphene, nitrogen-doped graphene, chemically functionalized graphene, or a combination thereof.

13. The process of claim 12, further comprising a step (e) of further heat-treating said humic acid film of merged or reduced HA or CHA at a second heat treatment temperature higher than the first heat treatment temperature for a sufficient period of time to produce a graphitic film having an inter-planar spacing $d_{002}$ less than 0.4 nm and an oxygen content or non-carbon element content less than 5% by weight; and (f) compressing said graphitic film to produce a highly conducting graphitic film having a physical density no less than 1.6 $g/cm^3$.

14. The process of claim 13, wherein said first volume fraction is equivalent to a weight fraction of from 0.05% to 3.0% by weight of HA or CHA in said dispersion.

15. The process of claim 13, wherein said step (e) of heat-treating induces chemical linking, merging, or chemical bonding of HA or CHA sheets with other HA or CHA sheets or with graphene sheets, or re-organization of a graphitic structure.

16. The process of claim 12, wherein said graphene sheets contain chemically functionalized graphene containing a chemical functional group selected from a polymer, $SO_3H$, COOH, $NH_2$, OH, R'CHOH, CHO, CN, COCl, halide, COSH, SH, COOR', SR', $SiR'_3$, $Si(-OR'-)_yR'_3-y$, $Si(-O-SiR'_2-)OR'$, R", Li, $AlR'_2$, Hg—X, $TlZ_2$ and Mg—X; wherein y is an integer equal to or less than 3, R' is hydrogen, alkyl, aryl, cycloalkyl, or aralkyl, cycloaryl, or poly(alkylether), R" is fluoroalkyl, fluoroaryl, fluorocycloalkyl, fluoroaralkyl or cycloaryl, X is halide, and Z is carboxylate or trifluoroacetate, or a combination thereof.

17. The process of claim 12, wherein said step (e) of heat-treating induces chemical linking, merging, or chemical bonding of HA or CHA sheets with other HA or CHA sheets, or re-organization of a graphitic structure.

18. The process of claim 1, wherein said HA or CHA sheets are in an amount sufficient to form a liquid crystal phase in said liquid medium.

19. The process of claim 18, wherein said dispersion is concentrated to contain higher than 3.0% but less than 15% by weight of HA or CHA dispersed in said liquid medium prior to said step (b).

20. The process of claim 1, wherein said dispersion contains a first volume fraction of HA or CHA dispersed in said liquid medium that exceeds a critical volume fraction ($V_c$) for a liquid crystal phase formation and said dispersion is concentrated to reach a second volume fraction of HA or CHA, greater than the first volume fraction, to improve a HA or CHA sheet orientation.

21. The process of claim 1, wherein said dispersion further contains a polymer dissolved in said liquid medium or attached to said HA or CHA.

22. The process of claim 1, wherein said CHA contains a chemical functional group selected from a polymer, $SO_3H$, COOH, $NH_2$, OH, R'CHOH, CHO, CN, COCl, halide, COSH, SH, COOR', SR', $SiR'_3$, $Si(-OR'-)_yR'_3-y$, $Si(-O-SiR'_2-)OR'$, R", Li, $AlR'_2$, Hg—X, $TlZ_2$ and Mg—X; wherein y is an integer equal to or less than 3, R' is hydrogen, alkyl, aryl, cycloalkyl, or aralkyl, cycloaryl, or poly(alkylether), R" is fluoroalkyl, fluoroaryl, fluorocycloalkyl, fluoroaralkyl or cycloaryl, X is halide, and Z is carboxylate or trifluoroacetate, or a combination thereof.

23. The process of claim 1, wherein said liquid medium consists of water and/or an alcohol.

24. The process of claim 1, wherein said liquid medium contains a non-aqueous solvent selected from polyethylene glycol, ethylene glycol, propylene glycol, an alcohol, a sugar alcohol, a polyglycerol, a glycol ether, an amine based solvent, an amide based solvent, an alkylene carbonate, an organic acid, or an inorganic acid.

25. The process of claim 1, wherein said highly oriented humic acid film has a thickness from 10 nm to 200 µm.

26. The process of claim 1, wherein said step (b) includes feeding a sheet of a solid substrate material from a roller to a deposition zone, depositing a layer of HA or CHA dispersion onto a surface of said sheet of solid substrate material to form said wet layer of HA or CHA dispersion thereon, drying said HA or CHA dispersion to form the dried HA or CHA layer deposited on said substrate surface, and collecting said HA or CHA layer-deposited substrate sheet on a collector roller.

27. The process of claim 1, wherein said first heat treatment temperature contains a temperature in the range of 100° C.-1,500° C. and the highly oriented humic acid film has an oxygen content less than 2.0%, an inter-planar spacing less than 0.35 nm, a physical density no less than 1.6 $g/cm^3$, a thermal conductivity of at least 800 W/mK, and/or an electrical conductivity no less than 2,500 S/cm.

28. The process of claim 1, wherein said first heat treatment temperature contains a temperature in the range of 1,500° C.-2,100° C. and the highly oriented humic acid film has an oxygen content less than 1.0%, an inter-planar spacing less than 0.345 nm, a thermal conductivity of at least 1,000 W/mK, and/or an electrical conductivity no less than 5,000 S/cm.

29. The process of claim 1, wherein the highly oriented humic acid film exhibits a degree of graphitization no less than 80% and/or a mosaic spread value less than 0.4.

30. The process of claim 1, wherein said highly oriented humic acid film contains chemically bonded hexagonal carbon planes that are parallel to one another.

31. The process of claim 1, wherein said HA or CHA sheets have a maximum original length and said highly oriented humic acid film contains HA or CHA sheets having a length larger than said maximum original length.

* * * * *